(12) United States Patent
Shearman et al.

(10) Patent No.: US 11,760,643 B2
(45) Date of Patent: Sep. 19, 2023

(54) DIAMOND COMPOSITION

(71) Applicant: Impossible Diamond, Inc., New York, NY (US)

(72) Inventors: Ryan Shearman, New York, NY (US); Daniel Wojno, New York, NY (US); Anthony W. Ippolito, Jr., New York, NY (US)

(73) Assignee: Impossible Diamond, Inc., New York, NY (US)

( * ) Notice: Subject to any disclaimer, the term of this patent is extended or adjusted under 35 U.S.C. 154(b) by 0 days.

(21) Appl. No.: 17/871,858

(22) Filed: Jul. 22, 2022

(65) Prior Publication Data
US 2023/0008358 A1  Jan. 12, 2023

Related U.S. Application Data

(63) Continuation-in-part of application No. 17/314,018, filed on May 6, 2021, now Pat. No. 11,371,162.

(60) Provisional application No. 63/225,365, filed on Jul. 23, 2021, provisional application No. 63/020,980, filed on May 6, 2020.

(51) Int. Cl.
  *C01B 32/26* (2017.01)
  *C07C 1/12* (2006.01)
  *A44C 17/00* (2006.01)
(52) U.S. Cl.
  CPC ............... *C01B 32/26* (2017.08); *C07C 1/12* (2013.01); *A44C 17/00* (2013.01); *C01P 2006/88* (2013.01)
(58) Field of Classification Search
  CPC . C01B 32/26; C07C 1/12; A44C 17/00; C01P 2006/88
  See application file for complete search history.

(56) References Cited

U.S. PATENT DOCUMENTS

| 2012/0051996 A1 | 3/2012 | Scarsbrook et al. |
| 2016/0230311 A1 | 8/2016 | Vince et al. |
| 2021/0095373 A1 | 4/2021 | Ballantine et al. |

FOREIGN PATENT DOCUMENTS

| IE | 911469 | * | 1/1992 |
| WO | 2021044140 A2 | | 3/2021 |
| WO | 2021226410 A1 | | 11/2021 |

OTHER PUBLICATIONS

International Search Report received in PCT/US22/38091 dated Dec. 8, 2022.

* cited by examiner

*Primary Examiner* — Thuan D Dang
(74) *Attorney, Agent, or Firm* — Run8 Patent Group; Peter Miller; Leah Raddatz

(57) ABSTRACT

One variation of a diamond composition includes carbon: including a first amount of carbon-13 isotopes and a second amount of carbon-12 isotopes; and sourced from a hydrocarbon mixture including hydrocarbons and formed via methanation of a carbon dioxide mixture. The carbon dioxide mixture: sourced from a sample of air including carbon dioxide and impurities; conveyed through a separation unit configured to remove impurities; including carbon dioxide and impurities; conveyed through a distillation column configured to regulate amounts of carbon-13 isotopes and carbon-12 isotopes; and exhibiting a target ratio of carbon-13 isotopes to carbon-12 isotopes at an outlet of the distillation column. The diamond composition: formed via chemical vapor deposition; and exhibiting an isotopic signature defining a final ratio of the first amount of carbon-13 isotopes to the second amount of carbon-12 isotopes within a first target range corresponding to the target ratio exhibited by the carbon dioxide mixture.

21 Claims, 10 Drawing Sheets

DIAMOND COMPOSITION

CROSS-REFERENCE TO RELATED APPLICATIONS

This application claims the benefit of U.S. Provisional Application No. 63/225,365, filed on 23 Jul. 2021, which is incorporated in its entirety by this reference.

This application is a continuation-in-part of U.S. patent application Ser. No. 17/314,018, filed on 6 May 2021, which claims the benefit of U.S. Provisional Application No. 63/020,980, filed on 6 May 2020, each of which is incorporated in its entirety by this reference.

TECHNICAL FIELD

This invention relates generally to the field of diamond synthesis and more specifically to a new and useful composition for a synthetic diamond in the field of diamond synthesis.

DESCRIPTION OF THE EMBODIMENTS

Figure 1:
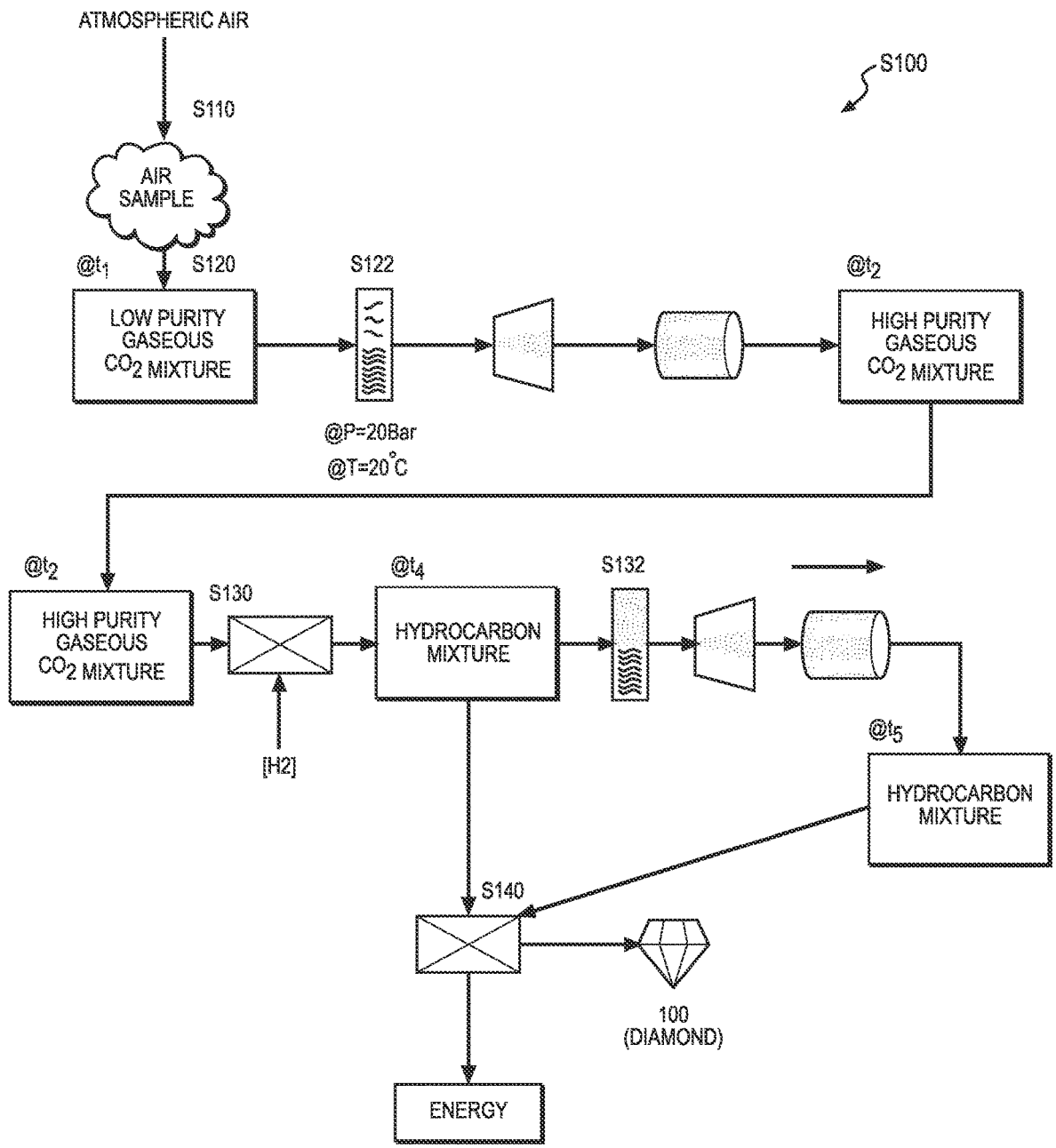
FIG. 1 is a flowchart representation of a method.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. COMPOSITION

A diamond composition 100 includes: a first amount (e.g., concentration) of carbon-13 isotopes; and a second amount of carbon-12 isotopes. The diamond composition 100 is formed via chemical vapor deposition and defines a ratio of the first amount of carbon-13 isotopes to the second amount of carbon-12 isotopes greater than −10.0 parts per thousand relative a Pee Dee Belemnite standard (hereinafter "parts-per-thousand-versus-PDB-standard").

One variation of the diamond composition 100 includes: a first amount of carbon-13 isotopes; and a second amount of carbon-12 isotopes. The diamond composition 100 includes carbon sourced from air and defines a ratio of the first amount of carbon-13 isotopes to the second amount of carbon-12 isotopes greater than −10.0 parts-per-thousand-versus-PDB-standard.

One variation of the diamond composition 100 includes: a first amount of carbon-13 isotopes; and a second amount of carbon-12 isotopes. The diamond composition 100 is formed via chemical vapor deposition and defines a ratio of the first amount of carbon-13 isotopes to the second amount of carbon-12 isotopes greater than −5.0 parts-per-thousand-versus-PDB-standard.

One variation of the diamond composition 100 includes: a first amount of carbon-13 isotopes; and a second amount of carbon-12 isotopes. The diamond composition 100 defines a ratio of the first amount of carbon-13 isotopes to the second amount of carbon-12 isotopes between −4.0 parts-per-thousand-versus-PDB-standard and −3.0 parts-per-thousand-versus-PDB-standard.

One variation of the diamond composition 100 includes: a first amount of carbon-13 isotopes; and a second amount of carbon-12 isotopes. The diamond composition 100 defines a ratio of the first amount of carbon-13 isotopes to the second amount of carbon-12 isotopes between −3.610 parts-per-thousand-versus-PDB-standard and −3.590 parts-per-thousand-versus-PDB-standard.

One variation of the diamond composition 100 includes carbon: sourced from air; including a first amount of carbon-13 isotopes; and including a second amount of carbon-12 isotopes. In this variation, the diamond composition 100 is formed via chemical vapor deposition of a diamond seed and exhibits an isotopic signature defining a first ratio of the first amount of carbon-13 isotopes to the second amount of carbon-12 isotopes within a first target range between −10.0 parts-per-thousand-versus-PDB-standard and 1.0 parts-per-thousand-versus-PDB-standard.

One variation of the diamond composition 100 includes carbon sourced from air and including a first amount of carbon-13 isotopes, a second amount of carbon-12 isotopes, and a third amount of carbon-14 isotopes. The diamond composition 100 is formed via chemical vapor deposition of a diamond seed and exhibits an isotopic signature defining a ratio of the first amount of carbon-13 isotopes to the second amount of carbon-12 isotopes within a target range between −4.0 parts-per-thousand-versus-PDB-standard and −3.0 parts-per-thousand-versus-PDB-standard.

One variation of the diamond composition 100: includes carbon sourced from air and including a first amount of carbon-13 isotopes and a second amount of carbon-12 isotope; is formed via chemical vapor deposition of a diamond seed exposed to a gaseous hydrocarbon mixture, the gaseous hydrocarbon mixture including hydrocarbons sourced from air and formed via methanation of a carbon dioxide mixture extracted from an air sample and including carbon dioxide and impurities (e.g., nitrogen); and exhibits an isotopic signature defining a first ratio of the first amount of carbon-13 isotopes to the second amount of carbon-12 isotopes exceeding a threshold ratio of −10.0 parts-per-thousand-versus-PDB-standard.

One variation of the diamond composition 100 includes carbon including a first amount of carbon-13 isotopes and a second amount of carbon-12 isotopes; and sourced from a hydrocarbon mixture including hydrocarbons and formed via methanation of a carbon dioxide mixture: sourced from a sample of air including carbon dioxide and a first concentration of impurities; conveyed through a separation unit configured to remove impurities from the carbon dioxide mixture; including carbon dioxide and a second concentration of impurities less than the first concentration of impurities at an outlet of the separation unit; conveyed through a distillation column configured to regulate amounts of carbon-13 isotopes and carbon-12 isotopes in the carbon dioxide mixture; and exhibiting a target ratio of carbon-13 isotopes to carbon-12 isotopes at an outlet of the distillation column. The diamond composition 100 is also formed via chemical vapor deposition of a diamond seed exposed to the hydrocarbon mixture and exhibits an isotopic signature defining a final ratio of the first amount of carbon-13 isotopes to the second amount of carbon-12 isotopes within a first target range corresponding to the target ratio exhibited by the carbon dioxide mixture.

2. METHOD

As shown in FIGS. 1, 4, 5, and 8-10 a method S100 for generating a synthetic (e.g., lab-grown) diamond includes: collecting an air sample including carbon dioxide and defining a first ratio of carbon-13 isotopes to carbon-12 isotopes in Block S110; extracting a carbon dioxide mixture from the air sample, the carbon dioxide mixture including carbon dioxide and defining a second ratio of carbon-13 isotopes to carbon-12 isotopes less than the first ratio in Block S120; reacting the carbon dioxide mixture with a stream of hydrogen, in the presence of a catalyst, to generate a hydrocarbon mixture including methane and defining a third ratio of carbon-13 isotopes to carbon-12 isotopes less than the second ratio in Block S130; exposing the hydrocarbon mixture to a diamond seed to generate a diamond composition 100 defining a fourth ratio of carbon-13 isotopes to carbon-12 isotopes greater than the first ratio in Block S140.

One variation of the method S100 for generating a synthetic (e.g., lab-grown) diamond includes: ingesting an air sample to extract a first carbon dioxide mixture including an amount of carbon dioxide and a first concentration of impurities (e.g., nitrogen), the amount of carbon dioxide defining a first ratio of carbon-13 isotopes to carbon-12 isotopes in Block S120; condensing the first carbon dioxide mixture via liquefaction to remove impurities from the first carbon dioxide mixture to generate a second carbon dioxide mixture including a second concentration of impurities less than the first concentration of impurities in Block S122; in a methanation reactor, mixing the second carbon dioxide with a stream of hydrogen, in the presence of a catalyst, to generate a hydrocarbon mixture including a third concentration of impurities (including carbon dioxide, hydrogen, and water) via methanation of the second carbon dioxide mixture in Block S130; and in a diamond reactor, exposing the hydrocarbon mixture to a diamond seed to generate a diamond composition 100 via chemical vapor deposition (or "CVD"), the diamond composition 100 defining a second ratio of carbon-13 isotopes to carbon-12 isotopes greater than the first ratio in Block S140.

One variation of the method S100 further includes condensing the hydrocarbon mixture via liquefaction to remove impurities from the hydrocarbon mixture to generate a secondary hydrocarbon mixture including a fourth concentration of impurities less than the third concentration of impurities in Block S132. In this variation, the method S100 includes, in the diamond reactor, exposing the secondary hydrocarbon mixture to the diamond seed to generate the diamond composition 100 via chemical vapor deposition in Block S140.

One variation of the method S100 includes: collecting an air sample including a first concentration of carbon dioxide and defining a first ratio of carbon-13 isotopes to carbon-12 isotopes in Block S110; extracting a carbon dioxide mixture from the air sample, the carbon dioxide mixture including a second concentration of carbon dioxide greater than the first concentration and a concentration of impurities and defining a second ratio of carbon-13 isotopes to carbon-12 isotopes less than the first ratio in Block S120; condensing the carbon dioxide mixture via liquefaction to reduce the concentration of impurities present in the carbon dioxide mixture in Block S122; reacting the carbon dioxide mixture with a stream of hydrogen, in the presence of a catalyst, to generate a hydrocarbon mixture including methane and defining a third ratio of carbon-13 isotopes to carbon-12 isotopes less than the second ratio in Block S130; and exposing the hydrocarbon mixture to a diamond seed within a diamond reactor to generate the diamond composition 100 via chemical vapor deposition, the diamond composition 100 defining a fourth ratio of carbon-13 isotopes to carbon-12 isotopes greater than the third ratio of carbon-13 isotopes to carbon-12 isotopes.

One variation of the method S100 includes: ingesting an air sample to extract a first carbon dioxide mixture including an amount of carbon dioxide and a first concentration of impurities (e.g., nitrogen), the amount of carbon dioxide defining a first ratio of carbon-13 isotopes to carbon-12 isotopes in Block S120; condensing the first carbon dioxide mixture via liquefaction to remove impurities from the first carbon dioxide mixture to generate a second carbon dioxide mixture including a second concentration of impurities less than the first concentration of impurities in Block S122; in a methanation reactor, mixing the second carbon dioxide with a stream of hydrogen, in the presence of a catalyst, to generate a hydrocarbon mixture including a third concentration of impurities (including carbon dioxide, hydrogen, and water) via methanation of the second carbon dioxide mixture, the hydrocarbon mixture defining a second ratio of carbon-13 isotopes to carbon-12 isotopes less than the first ratio in Block S130; and in a diamond reactor, exposing the hydrocarbon mixture to a diamond seed to generate a diamond composition 100 via chemical vapor deposition (or "CVD"), the diamond composition 100 defining a third ratio of carbon-13 isotopes to carbon-12 isotopes greater than the first ratio in Block S140.

One variation of the method S100 includes: harvesting a low-purity carbon dioxide mixture via direct air capture; transforming the low-purity carbon dioxide mixture into a high-purity hydrocarbon precursor via a methanation process; and generating a set of diamond crystals, formed of the diamond composition 100, from the high-purity hydrocarbon precursor to form a set of diamond products.

One variation of the method S100 includes: ingesting an air sample for collection of a first mixture from the air sample, the first mixture including carbon dioxide and a first concentration of impurities in Block S120; conveying the first mixture through a pressurized unit to promote liquefaction of the first mixture to generate a second mixture including carbon dioxide and a second concentration of impurities less than the first concentration of impurities in Block S122. The method S100 also includes conveying the second mixture through a distillation column to regulate an initial ratio of carbon-13 isotopes to carbon-12 isotopes present in the second mixture, at an inlet of the distillation column, to within: a first target range at a first outlet of the distillation column, defining a first outlet height, to generate a first fractionated mixture including carbon dioxide in Block S124; and a second target range at a second outlet of the distillation column, defining a second outlet height less than the first outlet height, to generate a second fractionated mixture including carbon dioxide, ratios within the second target range exceeding ratios within the first target range in Block S126. The method S100 further includes, during a first processing period: in a methanation reactor, mixing the first fractionated mixture with a first stream of hydrogen to generate a first hydrocarbon mixture including hydrocarbons in S134; and exposing the first hydrocarbon mixture to a first diamond seed within a diamond reactor to generate a first diamond including carbon and exhibiting a first ratio of carbon-13 isotopes to carbon-12 isotopes corresponding to the first target range in Block S142. The method S100 further includes, during a second processing period: in the methanation reactor, mixing the second fractionated mixture with a second stream of hydrogen to generate a second hydrocarbon mixture including hydrocarbons in Block S136; and exposing the second hydrocarbon mixture to a second diamond seed within the diamond reactor to generate a second diamond including carbon and exhibiting a second ratio of carbon-13 isotopes to carbon-12 isotopes exceeding the first ratio and corresponding to the second target range in Block S144.

One variation of the method S100 includes: collecting an air sample including a first concentration of carbon dioxide and exhibiting a first ratio of carbon-13 isotopes to carbon-12 isotopes in Block S110; extracting a first mixture from the air sample, the first mixture including a second concentration of carbon dioxide, greater than the first concentration of carbon dioxide, and a first concentration of impurities in Block S120; conveying the first mixture through a pressurized unit to promote liquefaction of the first mixture to generate a second mixture including carbon dioxide and a second concentration of impurities less than the first concentration of impurities in Block S122; conveying the second mixture through a distillation column to regulate a ratio of carbon-13 isotopes to carbon-12 isotopes present in the second mixture to within a target range at an outlet of the distillation column in Block S124; in a methanation reactor, mixing the second mixture with a stream of hydrogen to generate a third mixture including hydrocarbons in Block S130; and exposing the third mixture to a diamond seed within a diamond reactor to generate the diamond composition exhibiting a second ratio of carbon-13 isotopes to carbon-12 isotopes exceeding the first ratio and corresponding to the target range in Block S140.

In one variation, the method S100 further includes conveying the second mixture, collected from the outlet of the distillation column, through an absorption unit configured to remove impurities (e.g., nitrogen) from the second mixture in Block S126. In this variation, the method S100 includes, in the methanation reactor, mixing the second mixture, collected from an outlet of the absorption unit, with the stream of hydrogen to generate the third mixture including hydrocarbons in Block S130.

3. APPLICATIONS

Generally, the diamond composition 100 is an ethically-sourced, lab-grown, carbon-negative, jewelry-grade diamond. In particular, the method S100 can be executed to: directly capture a gaseous mixture of carbon dioxide and other components found in air (e.g., nitrogen, argon) from an air source (e.g., re-circulated air within a building, outdoor air, air pollution, human breath, a flu stack); to process this gaseous mixture of carbon dioxide and other components—according to various chemical techniques and/or in combination with additional components—to form a hydrocarbon mixture; and to further react this hydrocarbon mixture to form the diamond composition 100 (e.g., a jewelry-grade diamond). By implementing direct capture of a gaseous carbon dioxide mixture from air and transforming this mixture into a hydrocarbon precursor (i.e., the hydrocarbon mixture) for production of the diamond composition 100, the method S100 enables elimination of pollution, greenhouse gases, and mineral and water waste generated due to sourcing hydrocarbons (e.g., fossil fuels) directly from the ground via mining.

Further, the diamond composition 100 includes carbon isotopic concentrations similar to natural diamonds (e.g., ground-sourced diamonds). In particular, the diamond composition 100 defines a particular carbon isotopic signature (e.g., a ratio of carbon-13 isotopes to carbon-12 isotopes present in the diamond composition 100) within a similar range exhibited by natural diamonds (e.g., ground-sourced diamonds). Therefore, by sourcing carbon from the air—rather than the ground—the diamond composition 100 is less depleted in carbon-13 isotopes than traditional lab-grown diamonds (e.g., ground-sourced HPHT and/or CVD diamonds) which may be more heavily depleted in carbon-13.

This carbon isotopic signature can be leveraged to distinguish natural diamonds (e.g., ground-sourced diamonds) from traditional lab-grown diamonds by measuring carbon isotopic concentrations of these diamonds via mass spectroscopy in a standard carbon-13 test. For example, natural diamonds (e.g., ground-sourced diamonds) can exhibit carbon isotopic signatures within a target range (e.g., including greater than 95 percent of Peridotitic diamonds). Traditional lab-grown diamonds (e.g., ground-sourced HPHT and/or CVD diamonds) are more depleted in carbon-13 isotopes than natural diamonds (e.g., ground-sourced diamonds), and exhibit carbon isotopic signatures outside of this target range. These traditional lab-grown diamonds are therefore readily detectable as synthetic diamonds when subjected to the standard carbon-13 test. However, by sourcing carbon from atmospheric air—which is more enriched in carbon-13 isotopes—the diamond composition 100 can exhibit a carbon isotopic signature within this target range.

The diamond composition 100 is therefore indistinguishable from natural diamonds (e.g., ground-sourced diamonds), when subjected to the standard carbon-13 test, while detectably (e.g., via mass spectrometry) distinct from other lab-grown diamonds.

Further, the carbon isotopic signature of the diamond composition 100 can be predictably linked to a particular time period and location corresponding to collection of the original air sample from which carbon was extracted and transformed into this diamond composition 100. For example, a model linking carbon isotopic concentrations in ambient air to time period and location of air capture can be theoretically derived based on observed weather patterns (e.g., seasonal and geographic weather patterns).

This model can therefore predictably identify a time period (e.g., a season, a particular month) and/or location (e.g., a latitude) of air capture for a particular diamond, formed of the diamond composition 100 and generated via the method S100, based on the carbon isotopic signature of this particular diamond. For example, a user may purchase a diamond, formed of the diamond composition 100100, and generated from an air sample collected at a particular location (e.g., a geographic location). To determine a time period during which the air sample was collected, the user may access a carbon isotopic signature of her diamond, such as by bringing the diamond to a lab for testing. The user may then leverage an existing model linking carbon isotopic signature, air capture location, and air capture time period of diamonds formed of the diamond composition 100, to estimate the time period during which the air sample for her diamond was captured.

4. AIR TO DIAMOND

Generally, the diamond composition 100 can be generated by: directly capturing a gaseous mixture of carbon dioxide and other components found in air (e.g., nitrogen, argon, etc.) from an air source (e.g., re-circulated air within a building, outdoor air, air pollution, human breath); processing this gaseous mixture of carbon dioxide and other components—according to various chemical techniques and/or in combination with additional components—to form a hydrocarbon precursor; and reacting this hydrocarbon precursor (e.g., via chemical vapor deposition) to form the diamond composition 100, which can be configured to form a diamond product (e.g., a jewelry-grade diamond).

In particular, the method S100 includes: harvesting a low-purity carbon dioxide mixture via direct air capture (e.g., via amine filtration); transforming this low-purity mixture into a high-purity hydrocarbon precursor via a methanation process; and generating diamond crystals from this high-purity hydrocarbon precursor within a diamond reactor (e.g., a chemical vapor deposition reactor) to produce ethically-sourced, lab-grown, carbon-negative, jewelry-grade diamonds, such as described in U.S. patent application Ser. No. 17/314,012, filed on 6 May 2021, which is incorporated in its entirety by this reference.

4.1 Air to Carbon Dioxide Mixture

More specifically, Block S120 of the method S100 recites ingesting a first mixture (e.g., a low-purity carbon dioxide mixture) extracted from a first air sample (e.g., via amine filtration), the first mixture including carbon dioxide and a first concentration of impurities (e.g., nitrogen), the amount of carbon dioxide defining a first ratio of carbon-13 isotopes to carbon-12 isotopes. The resulting gaseous mixture (i.e., the first mixture) is a low-purity gaseous mixture of carbon dioxide (e.g., less than 80.0 percent carbon dioxide). This low-purity carbon dioxide mixture also includes concentrations of impurities found in air such as nitrogen, argon, and other gases.

In one implementation, the low purity, gaseous carbon dioxide mixture is extracted from atmospheric air via amine filtration. In particular, in this implementation, an air sample, including a first concentration of carbon dioxide, can be collected during an air capture period. An amount of carbon dioxide can then be extracted from the first air sample via filtration (e.g., amine filtration). This amount of carbon dioxide can then be heated, in a chamber, to generate a carbon dioxide mixture including a second concentration of carbon dioxide greater than the first concentration of carbon dioxide. This carbon dioxide mixture can then be stored in a container for further processing (e.g., at a second location). For example, air can be drawn into a reservoir (e.g., within a carbon capture device) defining an opening through which air enters the reservoir. The reservoir can include a filter arranged within the opening and configured to collect carbon dioxide molecules in the air flowing through the opening while enabling other particles in the air to flow through freely. Once the filter is saturated with carbon dioxide, the filter can be heated (e.g., to temperatures between 95 degrees Celsius and 120 degrees Celsius) to extract carbon dioxide gas from the filter. Upon heating the filter, the gaseous carbon dioxide mixture is released from the filter. This gaseous carbon dioxide mixture can then be collected and stored (e.g., in a container). Later, the gaseous carbon dioxide mixture (e.g., stored in the container) can be ingested for further processing.

In one implementation, direct air capture via amine filtration results in a low-purity gaseous carbon dioxide mixture exhibiting a carbon dioxide concentration between seventy percent and eighty-five percent. The low-purity gaseous carbon dioxide mixture exhibits an impurity concentration between fifteen percent and thirty percent, the impurity concentration including a concentration of nitrogen (e.g., in the form of NX compounds such as nitrogen oxides and/or ammonia). However, nitrogen can be toxic to diamond crystal growth if present in the diamond reactor. Therefore, this initial low purity gaseous carbon dioxide mixture can be further treated to increase the concentration of carbon dioxide and reduce the concentration of impurities in the mixture. In particular, the low purity gaseous carbon dioxide mixture can be purified via a liquefaction technique to reduce the concentration of nitrogen (e.g., in NX compounds) in the carbon dioxide mixture.

Furthermore, Block S122 of the method S100 recites: condensing the first carbon dioxide mixture via liquefaction to remove impurities from the first carbon dioxide mixture to generate a second carbon dioxide mixture including a second concentration of impurities less than the first concentration of impurities. In one implementation, the low purity gaseous carbon dioxide mixture is liquefied at low temperatures (e.g., less than 31 degrees Celsius) and with an applied pressure (e.g., less than 73 bar) to generate a higher purity liquid carbon dioxide mixture. The resulting higher purity liquid mixture of carbon dioxide therefore exhibits a greater concentration of carbon dioxide and lower concentration of impurities (e.g., nitrogen) than the input gaseous carbon dioxide mixture.

This high-purity carbon dioxide mixture—in a liquid state at an outlet of the separation unit—can then be converted from the liquid state to a gaseous state prior to methanation of the high-purity carbon dioxide mixture.

4.2 Methanation: Carbon Dioxide Mixture to Hydrocarbon Mixture

The methanation technique in Block S130 of the method S100 recites: in a methanation reactor, mixing the second carbon dioxide with a stream of hydrogen, in the presence of a catalyst, to generate a hydrocarbon mixture including a third concentration of impurities (including carbon dioxide, hydrogen, and water) via methanation of the second carbon dioxide mixture.

In one implementation, the high-purity gaseous carbon dioxide mixture (e.g., greater than 95 percent carbon dioxide concentration) is transferred to a methanation reactor configured to promote a catalytic methanation reaction. This methanation reactor system (e.g., the reactor and the high-purity gaseous carbon dioxide mixture) can be pressurized by introducing a stream of hydrogen gas to the system, which triggers methanation of the high-purity gaseous carbon dioxide mixture. In particular, in this implementation, the high-purity gaseous carbon dioxide mixture can be treated (e.g., mixed) with a stream of hydrogen (e.g., a stream of hydrogen gas), in the methanation reactor, in the presence of a catalyst, to generate a hydrocarbon precursor (e.g., hydrocarbon mixture) via methanation of the high-purity gaseous carbon dioxide mixture. The hydrocarbon precursor can include hydrocarbons (e.g., methane) and impurities such as hydrogen, carbon dioxide, and/or nitrogen (e.g., less than 350 parts-per-million, less than 10 parts-per-million, less than 2 parts-per-billion).

4.3 Chemical Vapor Deposition: Hydrocarbon Mixture to Diamond

Additionally, Block S140 of the method S100 recites: in a diamond reactor, exposing the hydrocarbon mixture to a diamond seed to generate a diamond composition 100 via chemical vapor deposition (or "CVD"), the diamond composition 100 defining a second ratio of carbon-13 isotopes to carbon-12 isotopes less than the first ratio. In particular, the high-purity hydrocarbon precursor can be transferred into a CVD reactor (e.g., a vacuum chamber) configured to generate diamond crystals via chemical vapor deposition. For example, a diamond seed can be placed in the CVD reactor. As the hydrocarbon precursor flows into the CVD reactor, the CVD reactor can be heated to very high temperatures (e.g., greater than Boo degrees Celsius). Heating the CVD reactor to these high temperatures causes carbon ions to dispel from the hydrocarbon precursor—which may layer into the diamond seed—thereby enabling the diamond seed to grow into a diamond (e.g., a rough diamond configured to be cut into one or more gemstones).

In one implementation, the high-purity hydrocarbon precursor enters the CVD reactor exhibiting a concentration of methane between 96.0 percent and 99.9999 percent. The CVD reactor can be tuned accordingly based on the concentration of methane and the concentration of impurities (e.g., hydrogen gas, carbon dioxide, argon, nitrogen) of the hydrocarbon precursor. For example, the temperature and pressure in the CVD reactor can be adjusted based on the concentration of methane in the hydrocarbon precursor.

Air present in the gaseous hydrocarbon mixture and CVD reactor can be purged from the CVD reactor to increase efficiency and yield of the reaction. In one implementation, air is purged from the CVD reactor by cycling an inert blend through the CVD reactor. For example, a stream of hydrogen gas can be cycled through the CVD reactor at set intervals throughout the CVD process. Similarly, a stream of an inert gas (e.g., argon) can be cycled through the CVD reactor to act as a carrier and therefore improve a rate of the reaction and a rate of diamond growth.

The CVD reactor can be configured to grow diamonds from a hydrocarbon precursor exhibiting a particular concentration of methane. Therefore, the flowrate of the hydrocarbon precursor into the CVD reactor can be adjusted to control a concentration of methane present in the CVD reactor. For example, if the hydrocarbon precursor exhibits a concentration of methane of 99.9 percent, the flowrate of the hydrocarbon precursor going into the CVD reactor can be lowered. However, if the hydrocarbon precursor exhibits a concentration of methane of 97 percent, then the flowrate of the hydrocarbon precursor going into the CVD reactor can be increased.

In one variation, a stream of hydrogen gas is cycled through the CVD reactor at a set flowrate based on the concentration of hydrogen gas in the hydrocarbon precursor. For example, if the hydrocarbon precursor exhibits a concentration of methane of 99.99 percent and thus a concentration of impurities—including hydrogen gas and carbon dioxide—of 0.01 percent, a stream of hydrogen gas can be cycled through the CVD reactor at a first flowrate based on the relatively low concentration of hydrogen gas present in the hydrocarbon precursor (and the CVD reactor). However, if the hydrocarbon precursor exhibits a concentration of methane of 97 percent and thus a concentration of impurities below 3 percent, a stream of hydrogen gas can be cycled through the CVD reactor at a second flowrate less than the first flowrate based on the relatively high concentration of hydrogen gas already present in the hydrocarbon precursor (and the CVD reactor).

The growth rate of the diamonds in the CVD reactor can be adjusted based on: the concentration of methane in the hydrocarbon precursor entering the CVD reactor; the flow rate of the hydrocarbon precursor can be adjusted to alter the growth rate of the diamonds; and/or the temperature within the CVD reactor.

Figure 4:
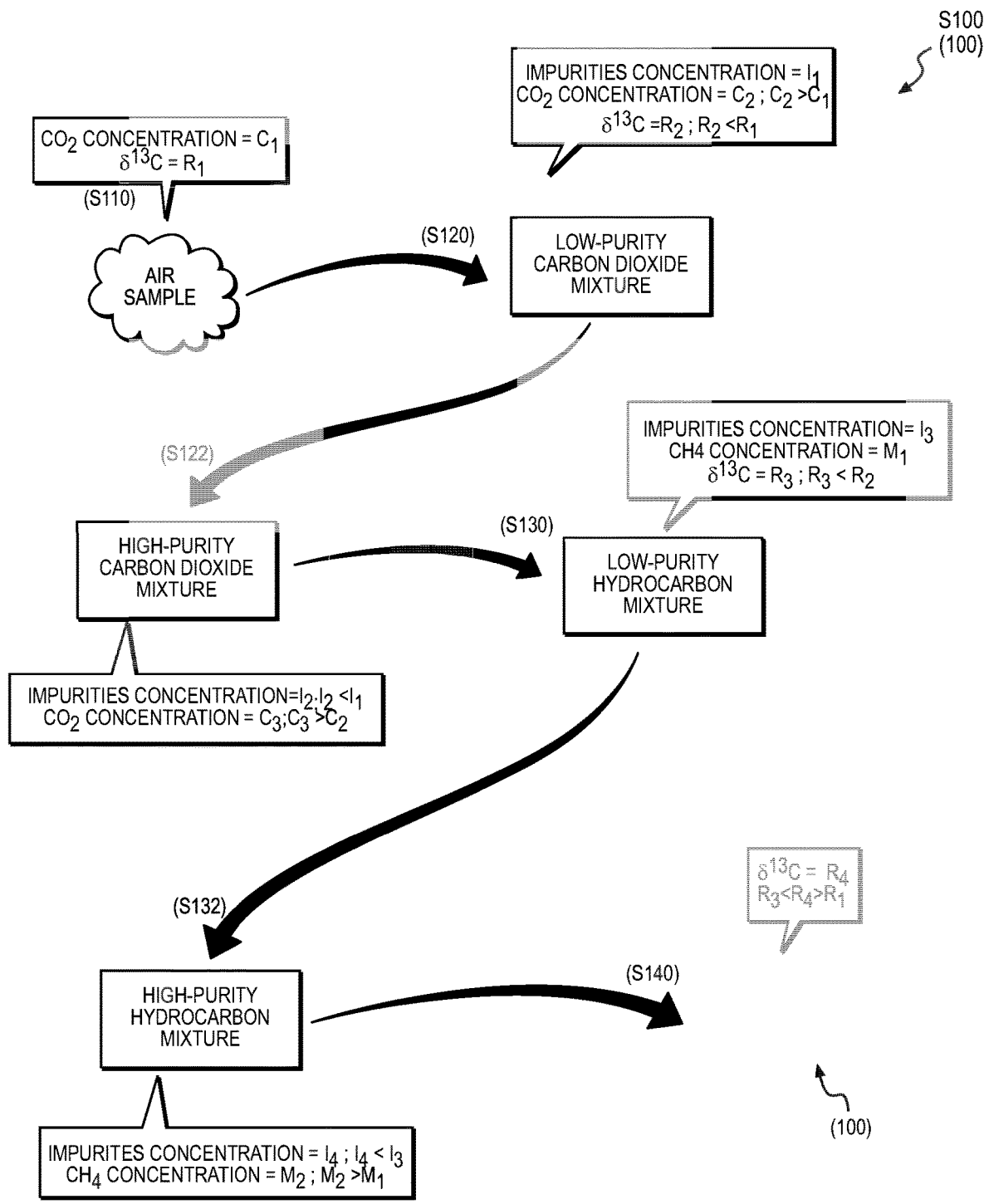
FIG. 4 is a flowchart representation of one variation of the method.
Figure 5:
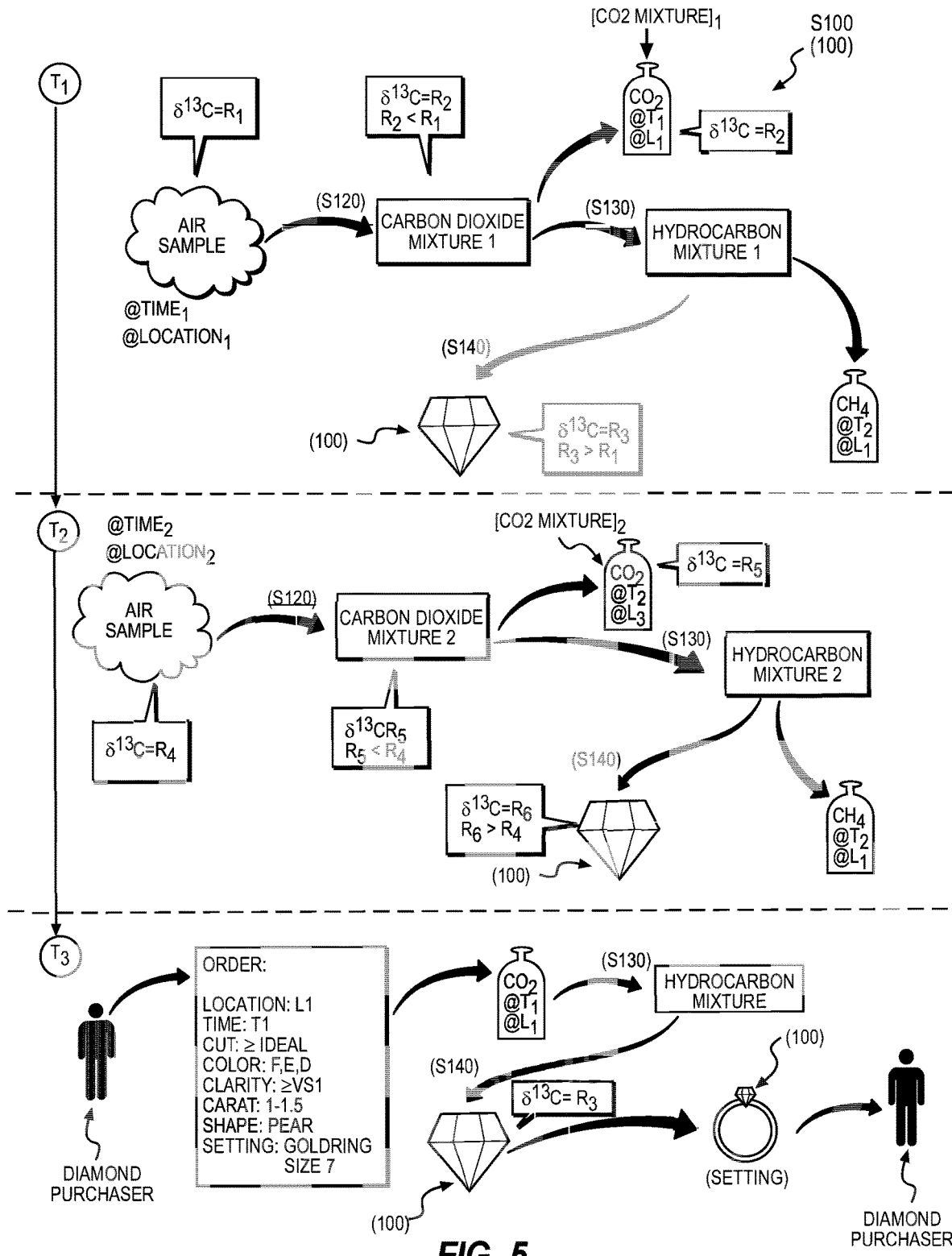
FIG. 5 is a flowchart representation of one variation of the method.

Therefore, the method S100 can be executed to: extract a carbon dioxide mixture from atmospheric air; convert the carbon dioxide mixture to a hydrocarbon mixture via methanation; and generate diamonds of sufficient quality (e.g., clarity, color, cut, carat weight, type) with particular characteristics (e.g., size, shape, number, position, nature, grade, etc.) that can be inserted into a setting (e.g., jewelry, ornamental setting, decorative setting) to form a diamond product wearable by a user via a carbon-negative process from this carbon dioxide mixture. For example, the diamond composition 100 can form a diamond configured to insert into an ornamental setting to form a diamond product wearable by a user. In another example, the diamond composition 100 can form a diamond exhibiting a type IIA diamond type and configured to insert into a jewelry setting to generate a diamond product wearable by the user. In yet another example, the diamond composition forms a diamond configured to insert into a jewelry setting to generate a diamond product wearable by the user, as shown in FIGS. 4 and 5.

4.4 Distillation: Regulating the Isotopic Ratio of Carbon-13 to Carbon-12

In one variation, the carbon dioxide mixture can be fed through a distillation column—configured to separate components of the carbon dioxide mixture based on weight of these components—to regulate amounts of carbon-13 isotopes and carbon-12 isotopes present in the carbon dioxide mixture, prior to mixing of the carbon dioxide mixture with the stream of hydrogen in the methanation reactor.

In particular, the carbon dioxide mixture—exhibiting an initial ratio of carbon-13 isotopes to carbon-12 isotopes at an inlet of the distillation column—can be fed into the inlet of the distillation column and collected from a particular outlet of the distillation column (e.g., an upper outlet proximal a top of the distillation column, a lower outlet proximal a bottom of the distillation column), such that the resulting carbon dioxide mixture, collected at the particular outlet, exhibits a ratio of carbon-13 isotopes to carbon-12 isotopes within a target range. For example, a first stream of the carbon dioxide mixture—collected from an upper outlet proximal a top of the distillation column—can exhibit a first ratio of carbon-13 isotopes to carbon-12 isotopes within a first target range (e.g., less than −40.0 parts-per-thousand-versus-PDB-standard). Additionally and/or alternatively, in this example, a second stream of the carbon dioxide mixture—collected from a lower outlet proximal a bottom of the distillation column—can exhibit a second ratio of carbon-13 isotopes to carbon-12 isotopes within a second target range (e.g., greater than −10.0 parts-per-thousand-versus-PDB-standard), ratios of carbon-13 isotopes to carbon-12 isotopes within the second target range greater than ratios of carbon-13 isotopes to carbon-12 isotopes within the first target range.

Therefore, in this variation, by regulating the ratio of carbon-13 isotopes to carbon-12 isotopes of the carbon dioxide mixture to within a particular target range, the diamond composition—formed via chemical vapor deposition of the hydrocarbon mixture generated via methanation of the carbon dioxide mixture—can be configured to exhibit a final ratio of carbon-13 isotopes to carbon-12 isotopes corresponding to the particular target range.

In one implementation: the carbon dioxide mixture can be converted into a liquid carbon dioxide mixture via liquefaction, as described above, and this liquid carbon dioxide mixture can be conveyed through the distillation column to regulate amounts of carbon-13 isotopes and carbon-12 isotopes. At an inlet of the distillation column, the liquid carbon dioxide mixture exhibits an initial ratio of carbon-13 isotopes to carbon-12 isotopes. At an outlet of the distillation column, the liquid carbon dioxide mixture exhibits a ratio of carbon-13 isotopes to carbon-12 isotopes within a target range.

More specifically, at the outlet of the distillation column, an amount of the liquid carbon dioxide mixture can be collected and exhibits a ratio of carbon-13 isotopes to carbon-12 isotopes within a target range. Further, the carbon dioxide mixture—collected from the outlet of the distillation column—can be conveyed through an absorption unit to remove impurities (e.g., nitrogen) present in the carbon dioxide mixture, such as in response to the concentration of impurities in the carbon dioxide mixture exceeding a threshold concentration of impurities (e.g., one percent, five percent). The resulting carbon dioxide mixture can therefore: exhibit a ratio of carbon-13 isotopes to carbon-12 isotopes within the target range; include a concentration of impurities less than the threshold concentration of impurities; and include a concentration of carbon dioxide exceeding a threshold concentration of carbon dioxide (e.g., 95 percent, 99 percent).

In one implementation, Blocks S124 and S126 of the method S100 recite: conveying the second mixture through a distillation column to regulate an initial ratio of carbon-13 isotopes to carbon-12 isotopes present in the second mixture, at an inlet of the distillation column, to within: a first target range at a first outlet of the distillation column, defining a first outlet height, to generate a first fractionated mixture including carbon dioxide; and a second target range at a second outlet of the distillation column, defining a second outlet height less than the first outlet height, to generate a second fractionated mixture including carbon dioxide, ratios within the second target range exceeding ratios within the first target range. In this step, the second mixture (e.g., high purity carbon-dioxide mixture) is conveyed through a distillation column to regulate the ratio of carbon-13 isotopes to carbon-12 isotopes present in the resulting fractionated mixture to within a target range corresponding to an outlet height of the distillation column.

In one implementation, gravity sorts the second mixture by weight—such that the heaviest impurities (e.g., carbon-13 isotopes, nitrogen) sink to the base of the distillation column and the lightest impurities (e.g., carbon-12 isotopes) float to the top of the distillation column—to generate a fractionated mixture, including carbon dioxide, exhibiting a controlled ratio of carbon 13-isotopes to carbon-12 isotopes within a target range. In particular, at a maximum outlet height of the distillation column, the target range represents a high purity fractionated mixture (e.g., lower concentration of impurities) including a relatively high concentration of carbon-12 isotopes and a relatively low concentration of carbon-13 isotopes. Alternatively, at a minimum outlet height of the distillation column, the target range represents a less pure fractionated mixture (e.g., higher concentration of impurities), including a relatively low concentration of carbon-12 isotopes and a relatively high concentration of carbon-13 isotopes.

For example, a first fractionated mixture can be collected at the maximum outlet height of the distillation column and exhibit a first ratio of carbon-13 isotopes to carbon-12 isotopes within a first target range (e.g., between −60 parts-per-thousand-versus-PDB-standard and −20 parts-per-thousand-versus-PDB-standard). During a first processing period in a methanation reactor, the first fractionated mixture (e.g., high purity fractionated mixture) can be mixed with a first stream of hydrogen to generate a first hydrocarbon mixture including hydrocarbons (e.g., via methanation). Then, the first hydrocarbon mixture can be exposed to a first diamond seed within a diamond reactor to generate a first diamond including carbon (e.g., via chemical vapor deposition) and exhibiting a first ratio of carbon-13 isotopes to carbon-12 isotopes (e.g., less than −10 parts-per-thousand-versus-PDB-standard, less than −20 parts-per-thousand-versus-PDB-standard, less than −50 parts-per-thousand-versus-PDB-standard) corresponding to the first target range.

Similarly, a second fractionated mixture can be collected at the minimum outlet height of the distillation column and exhibit a second ratio of carbon-13 isotopes to carbon-12 isotopes within a second target range (e.g., between −12 parts-per-thousand-versus-PDB-standard and 0 parts-per-thousand-versus-PDB-standard). During a second processing period in the methanation reactor, the second fractionated mixture (e.g., less pure fractionated mixture) can be mixed with a second stream of hydrogen to generate a second hydrocarbon mixture including hydrocarbons (e.g., via methanation). Then, the second hydrocarbon mixture can be exposed to a second diamond seed within the diamond reactor to generate a second diamond including carbon and exhibiting a second ratio of carbon-13 isotopes to carbon-12 isotopes (e.g., exceeding −10 parts-per-thousand-versus-PDB-standard, exceeding −5 parts-per-thousand-versus-PDB-standard, exceeding 0 parts-per-thousand-versus-PDB-standard) exceeding the first ratio and corresponding to the second target range.

4.4.1 Mixing Fractionated Carbon Dioxide Mixtures

In one variation, subvolumes of the carbon dioxide mixture—collected from different outlets (e.g., at different heights) of the distillation column can be mixed to generate a volume of the carbon dioxide mixture exhibiting a target ratio of amounts of carbon-13 isotopes to carbon-12 isotopes.

For example, a first subvolume of the carbon dioxide mixture can be collected from a first outlet of the distillation column—defining a first outlet height—and exhibit a first ratio of carbon-13 isotopes to carbon-12 isotopes. Then, a second subvolume of the carbon dioxide mixture can be collected from a second outlet of the distillation column—defining a second outlet height lower than the first outlet height—and exhibit a second ratio of carbon-13 isotopes to carbon-12 isotopes. Later, the first subvolume of carbon dioxide and the second subvolume of carbon dioxide can be mixed together to generate a volume of the carbon dioxide mixture exhibiting a target ratio of carbon-13 isotopes to carbon-12 isotopes. The resulting volume of the carbon dioxide mixture can be generated without adjusting positions of the outlets and/or parameters of the distillation column.

Alternatively, batches of each subvolume of the carbon dioxide mixture—collected from each outlet of the distillation column (e.g., first outlet defining the first outlet height and second outlet defining the second outlet height lower than the first outlet height)—can be stored at a facility. Later, the first subvolume and the second subvolume can be mixed to generate a volume of the carbon dioxide mixture exhibiting a target ratio of carbon-13 isotopes to carbon-12 isotopes. Thus, mixing the subvolumes of the carbon dioxide mixture can yield a volume of the carbon dioxide mixture exhibiting a particular (e.g., desired) ratio of carbon-13 isotopes to carbon-12 isotopes.

Therefore, subvolumes of the carbon dioxide mixture can be mixed together in real-time to generate volumes of the carbon dioxide mixture that exhibit a range of target ratios of carbon-13 isotopes to carbon-12 isotopes. Alternatively, volumes of the carbon dioxide mixture can also be generated post-hoc by storing batches of each subvolume of the carbon dioxide mixture for future mixing to yield a particular ratio of carbon-13 isotopes to carbon-12 isotopes.

4.5 Location-Based Air Capture

In one implementation, the diamond composition 100 can be generated from a low-purity carbon dioxide mixture extracted from air from a particular location or place of significance (e.g., to the diamond owner), such that the diamond composition 100 can be linked to the particular location. For example, a couple may purchase an engagement ring with a diamond, formed of the diamond composition 100, generated from carbon that is sourced from air in a location of significance to the couple (e.g., a place where the couple met, a place where the couple vacationed). In another example, players on a championship football team may receive rings with diamonds, formed of the diamond composition 100, generated from carbon sourced from air in the stadium at which the championship game was played. In this example, a mobile carbon capture device can be deployed to the stadium prior to a start of the championship game. The mobile carbon capture device can be configured to capture air (e.g., carbon dioxide, nitrogen, argon, etc.) inside the stadium and store the resulting low-purity carbon dioxide mixture within a tank on the mobile carbon capture device. Later, when the mobile carbon capture device returns to the lab, the low-purity mixture can be purified and treated as described above to generate the diamond composition 100 from carbon extracted from the air in the stadium during the championship game.

Figure 7:
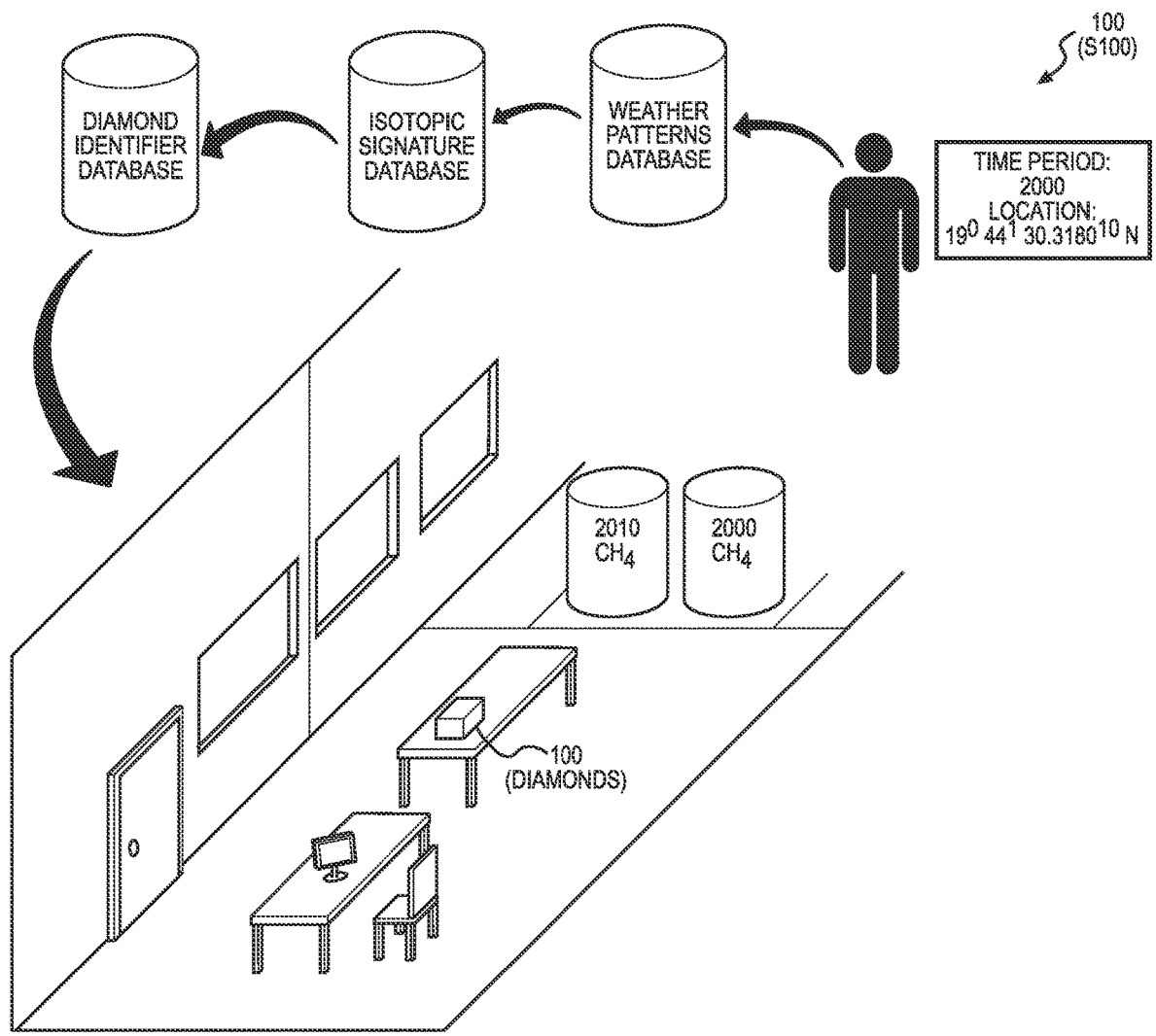
FIG. 7 is a schematic representation of a diamond composition.
Figure 7:
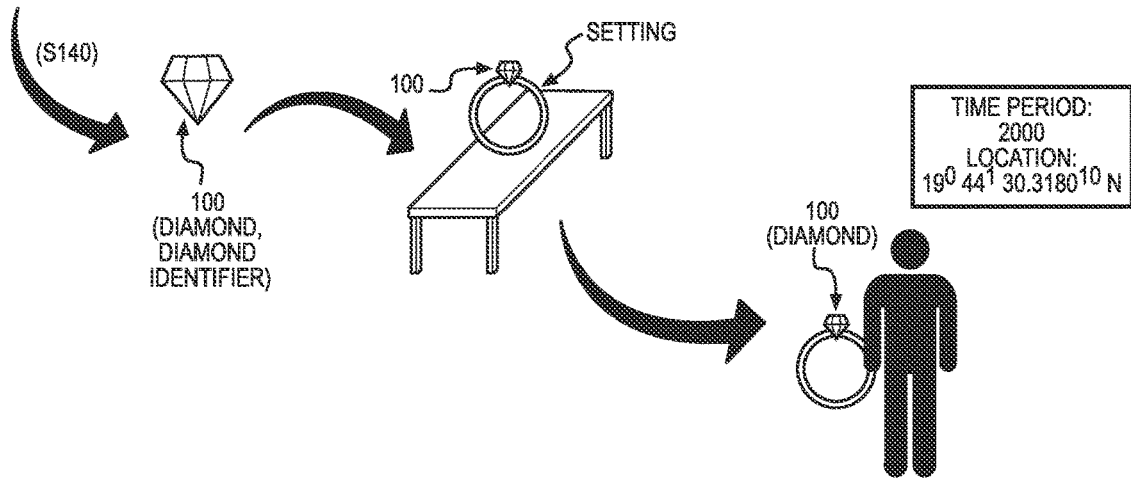

Additionally, in this implementation, each diamond—formed of the diamond composition 100 (e.g., produced via the method S100)—can be identified via a diamond identifier (e.g., a serial number). This serial number can be linked to the location, region, or place from which carbon for a particular diamond was extracted, such that diamond owners or diamond purchasers may have access to this location, as shown in FIG. 7.

For example, the diamond composition 100 can be generated via the method S100 and include carbon sourced from air captured at a target location. Upon generation of a diamond formed of the diamond composition, the diamond can be engraved with a diamond identifier (e.g., a serial number, a barcode) assigned to the diamond and associated with the target location. In particular, in this example, the diamond identifier can be stored in a diamond identifier database and linked to the target location within this diamond identifier database. Later, when a user purchases the diamond, the user may search the diamond identifier database—such as by entering or scanning the diamond identifier engraved on the diamond—to identify the target location corresponding to air capture for this particular diamond purchased by the user.

Figure 9:
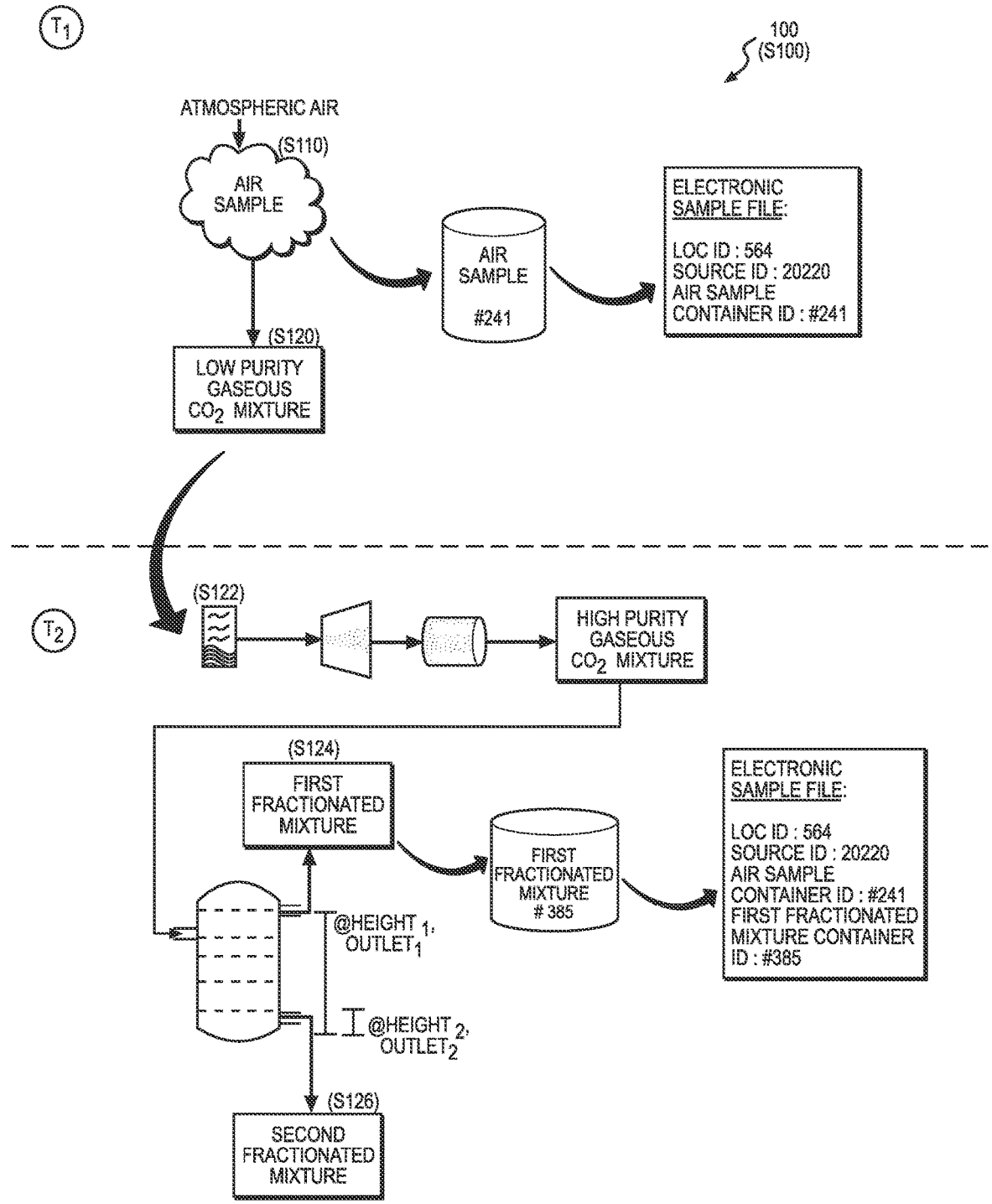
FIG. 9 is a flowchart representation of one variation of the method.

In one variation, the diamond composition 100 can be generated from a carbon dioxide mixture extracted from an air sample collected during a particular time period and at a target location such that the diamond composition 100 can be linked to the target location via a diamond identifier (e.g., serial number). For example, an air sample can be collected at a target location during an air capture period and stored in a first container. Then a computer system/model can: generate an electronic sample file; write a location identifier for the target location to the electronic sample file; write a first time value corresponding to the air capture period to the electronic sample file; link a first identifier arranged on the first container to the electronic sample file; and—upon generation of a first diamond from this air sample stored in the first container—write a first diamond identifier (e.g., serial number), corresponding to the first diamond formed of the diamond composition 100, to the electronic sample file, as shown in FIG. 9. Thus, the diamond composition 100 can be linked to the target location via the diamond identifier (e.g., serial number).

Subsequently, diamond purchasers may access a diamond identifier database, searchable by diamond identifiers (e.g., serial numbers) of diamonds. Upon entering a particular serial number, a diamond purchaser may identify the location from which the carbon was sourced for a diamond corresponding to this serial number. Additionally, a future diamond purchaser may search the database by location to identify a set of diamonds, formed of the diamond composition 100, generated from carbon sourced from a particular location.

4.6 Time-Based Air Capture

Figure 6:
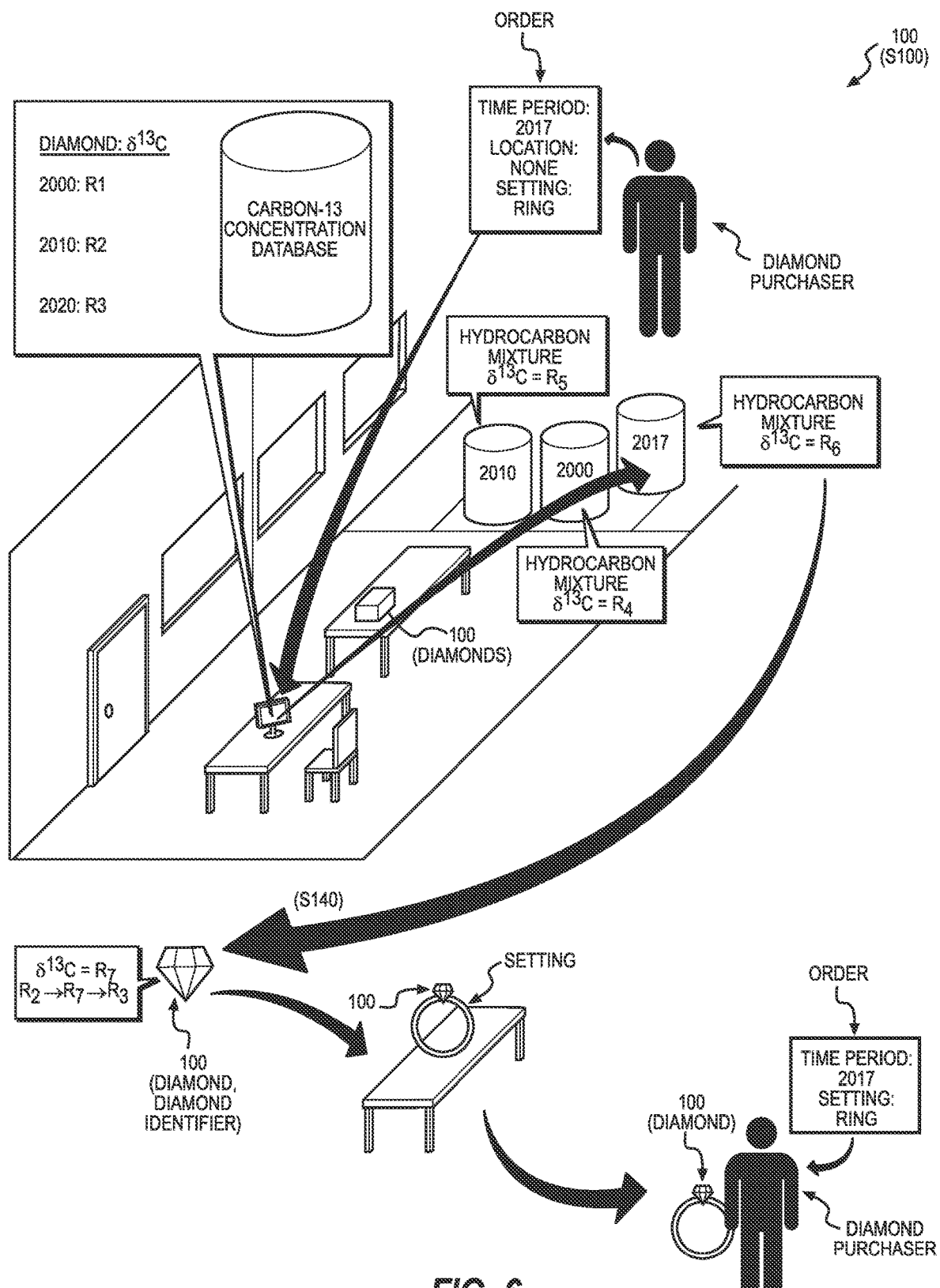
FIG. 6 is a schematic representation of a diamond composition.

As shown in FIG. 6, the diamond composition 100 can be generated from a low-purity carbon dioxide mixture extracted from air during a particular time period or at a time of significance (e.g., to the diamond owner), such that the diamond composition 100 can be linked to the particular time period.

Furthermore, carbon sourced from air during the particular time period (e.g., 2022) can be stored in a facility such that diamonds formed of the diamond composition 100 from this carbon can be reproduced in the future. In particular, the carbon dioxide mixture (e.g., the low-purity carbon dioxide mixture, the high-purity carbon dioxide mixture)—extracted from an air sample collected during the particular time period—and/or the hydrocarbon mixture—formed during methanation of the carbon dioxide mixture—can be stored (e.g., in the facility), such that diamonds can be generated via the method S100 and/or reproduced in the future from carbon dioxide and/or hydrocarbon mixtures including carbon sourced from air during a preceding time period. Alternatively, the diamond composition 100 can be generated via the method S100 during the particular time period (e.g., 2022).

For example, a couple may purchase an engagement ring with a diamond, formed of the diamond composition 100, generated from carbon that is sourced from air at a time of significance to the couple (e.g., a year when the couple met, a year when the couple got married). In another example, a couple may purchase a necklace for their child, formed of the diamond composition 100, generated from carbon that is sourced from air at a time of significance to the couple (e.g., a year when the child was born, a year when the child graduated from high school, a year when the child graduated from college).

Additionally, in this implementation, each diamond—formed of the diamond composition 100 (e.g., produced via the method S100)—can be identified via the carbon-13 concentration and/or isotopic signature of the diamond. This carbon-13 concentration can be linked to the time period from which carbon for a particular diamond was extracted, such that diamond owners or diamond purchasers may have access to this time period.

Subsequently, a person may be gifted with a set of diamond earrings and may want to discover when the diamonds in the set of diamond earrings were produced. The person can take the set of diamond earrings to any laboratory (e.g., analytical chemistry laboratory) for carbon-13 concentration analysis of the diamonds via mass spectrometry. The person can then leverage the carbon-13 concentration and enter a query for this carbon-13 concentration in a database that links carbon-13 concentrations of diamonds with the particular time period in which the carbon sourced from air was extracted. Thus, the person can discover the particular time period in which the diamonds in the set of diamond earrings were produced.

In another implementation, the diamond composition 100 can be generated from a carbon dioxide mixture extracted from air—during a target time period (e.g., air capture period)—and conveyed through a distillation column, such that the diamond composition 100 can be linked to the target time period.

For example, a first volume of the carbon dioxide mixture is collected from an outlet of the distillation column at a first outlet height, in a set of outlet heights, during a target time period. Then, the carbon dioxide mixture can form a hydrocarbon mixture via the methanation process and generate a diamond via the CVD process. The diamond composition 100 forms a diamond defining a diamond identifier engraved in the diamond and configured to associate the diamond with the target time period via a model, the model configured to link the diamond identifier to the first target ratio of carbon-13 isotopes to carbon-12 isotopes and to the target time period.

5. CARBON ISOTOPIC SIGNATURE

Generally, stable isotopic compositions of light (e.g., low mass) elements—such as carbon, Oxygen, hydrogen, nitrogen, Sulfur etc.—are reported as "delta" (d) values in parts per thousand (i.e., per mil, ‰; per mill, ‰; or per mille, ‰) enrichments or depletions relative to a standard known composition (or "established reference material"). The standard for carbon stable isotopes is the Pee Dee Belemnite standard (or "PDB standard").

The diamond composition 100 can include a mixture of carbon isotopes (e.g., carbon-13 isotopes and carbon-12 isotopes and/or carbon-14 isotopes) defining a particular isotopic signature (or "$\delta^{13}C$"). This particular isotopic signature is a measure of the ratio of stable isotopes (e.g., carbon-13 isotopes and carbon-12 isotopes) of the diamond composition 100. Additionally, the isotopic signature is reported as a "delta" (d) value in parts-per-thousand-versus-PDB-standard (e.g., −10.0 parts-per-thousand-versus-PDB-standard, 1 parts-per-thousand-versus-PDB-standard), as described below.

5.1 Variations in Carbon Isotope Concentration

In one implementation, the diamond composition 100 can include carbon isotopic concentrations similar to natural diamonds (e.g., ground-sourced diamonds). By sourcing carbon from the air—rather than the ground—the diamond composition 100 is less depleted in carbon-13 than traditional lab-grown diamonds (e.g., ground-sourced HPHT and/or CVD diamonds) which may be more heavily depleted in carbon-13 compared to the diamond composition 100 and natural diamonds (e.g., ground-sourced diamonds).

Figure 2:
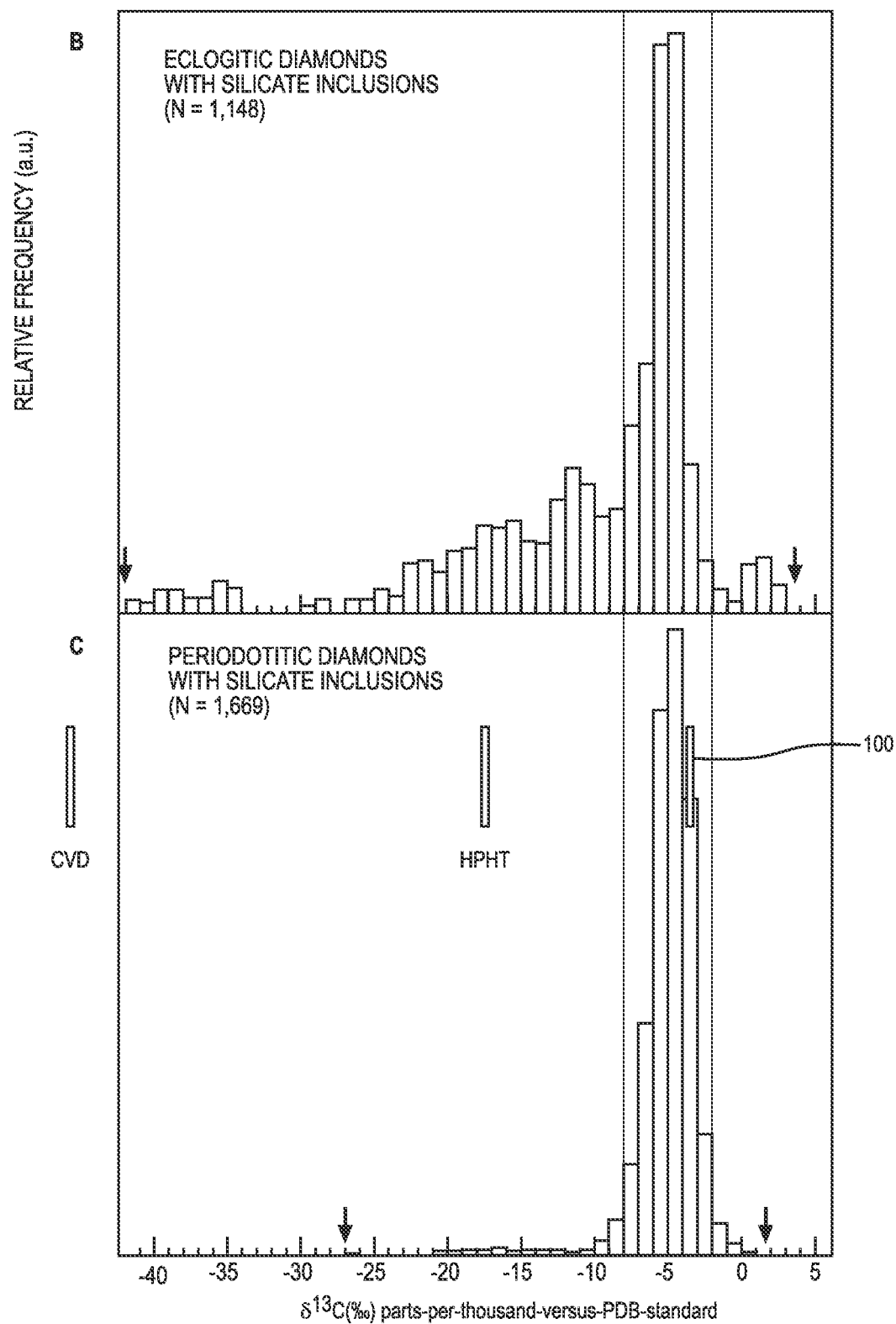
FIG. 2 is a graphical representation of a diamond composition.
Figure 3:
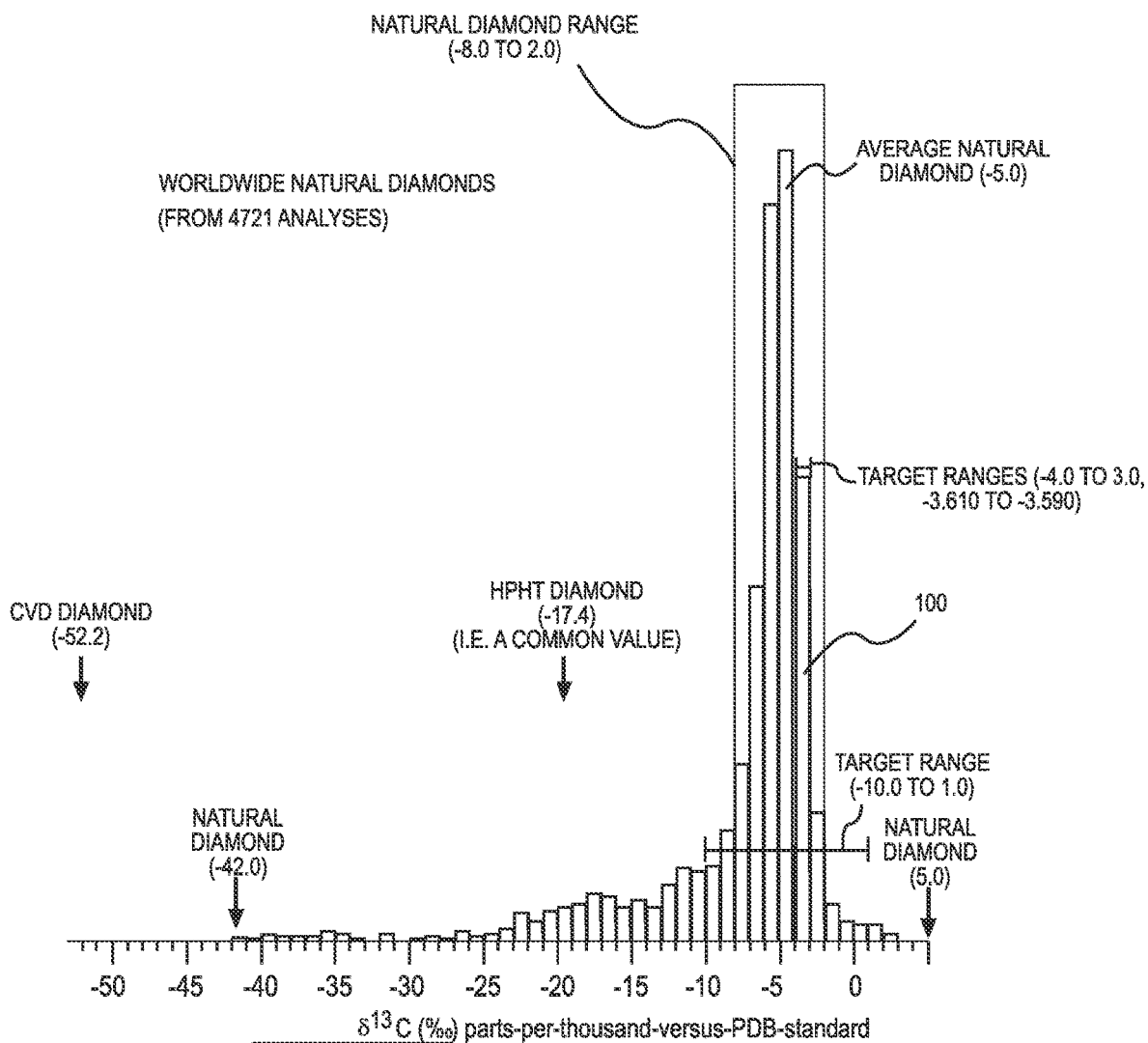
FIG. 3 is a graphical representation of a diamond composition.

In particular, natural diamonds (e.g., ground-sourced diamonds) are more enriched in carbon-13 than traditional lab-grown diamonds due to natural decaying of carbon-14 isotopes into carbon-13 isotopes over time. Alternatively, traditional lab-grown diamonds, including carbon sourced from the ground, are sourced in the form of hydrocarbons (e.g., organic carbon) and are more depleted in carbon-13 than natural diamonds (e.g., ground-sourced diamonds). For example, a traditional lab-grown CVD diamond is formed in a chemical vapor deposition reactor from hydrocarbons sourced from the ground. These hydrocarbons include a greater proportion of organic carbon than inorganic carbon, which is more depleted in carbon-13 than inorganic carbon. After chemical vapor deposition of these hydrocarbons, the resulting CVD diamonds include more organic carbon than inorganic carbon. More specifically, a natural, ground-sourced diamond includes a greater proportion of inorganic carbon than organic carbon, which is less depleted in carbon-13 than organic carbon, compared to a standard CVD diamond (e.g., a lab-grown CVD diamond). Therefore, the CVD diamonds exhibit greater carbon-13 depletion, and thus a more negative carbon isotopic signature than most natural diamonds (e.g., ground-sourced diamonds), as shown in FIGS. 2 and 3. For example, as shown in FIG. 3, a natural diamond can exhibit an average isotopic signature—defining a ratio of an amount of carbon-13 isotopes to an amount of carbon-12 isotopes—of −5.0 parts-per-thousand-versus-PDB-standard. Alternatively, a CVD diamond can exhibit an isotopic signature of −52.2 parts-per-thousand-versus-PDB-standard.

Alternatively, a diamond formed of the diamond composition 100 via execution of Blocks of the method S100—including chemical vapor deposition of hydrocarbons including carbon sourced from air—can be configured to exhibit a similar ratio of carbon-13 isotopes to carbon-12 isotopes as a natural diamond (e.g., ground-sourced diamond). In particular, the diamond composition 100 can include carbon sourced from air and including a first amount of carbon-13 isotopes and a second amount of carbon-12 isotopes. The diamond composition 100 can be formed via CVD of a diamond seed and can exhibit an isotopic signature defining a first ratio of the first amount of carbon-13 isotopes to the second amount of carbon-12 isotopes within a target range (e.g., between −10.0 parts-per-thousand-versus-PDB-standard and 1.0 parts-per-thousand-versus-PDB-standard, between 8.0-parts-per-thousand-versus-PDB-standard and −2.0 parts-per-thousand-versus-PDB-standard) corresponding to (e.g., including, within a threshold deviation of) ratios of amounts of carbon-13 isotopes to carbon-12 isotopes exhibited by natural diamonds (e.g., ground-sourced diamonds). Thus, the isotopic ratio of the diamond composition 100 can fall within a target range configured to match and/or overlap with isotopic ratios of natural diamonds (e.g., ground-sourced diamonds). Further, the diamond composition 100 can be configured to exhibit this isotopic signature defining the first ratio within the target range, such that ratios within the target range exceed ratios exhibited by standard CVD diamonds.

In one example, the diamond composition 100 is formed via CVD of a diamond seed exposed to a gaseous hydrocarbon mixture—including hydrocarbons including carbon sourced from air—formed via methanation of a carbon dioxide mixture extracted from a sample of air and including carbon dioxide and impurities. The diamond composition 100 can exhibit an isotopic signature defining a first ratio of the first amount of carbon-13 isotopes to the second amount of carbon-12 isotopes exceeding a threshold ratio of −10.0 parts-per-thousand-versus-PDB-standard. In particular, the carbon dioxide mixture can exhibit an initial ratio of initial amounts of carbon-13 isotopes to carbon-12 isotopes and the gaseous hydrocarbon mixture can exhibit a secondary ratio of secondary amounts of carbon-13 isotopes to carbon-12 isotopes, the secondary ratio less than the initial ratio of the carbon dioxide mixture. The resulting diamond composition 100—formed via CVD of the gaseous hydrocarbon mixture—can then exhibit the first ratio greater than the initial ratio of the carbon dioxide mixture and the secondary ratio of the gaseous hydrocarbon mixture.

In the preceding example, a sample of atmospheric air can exhibit a first isotopic ratio of carbon-13 isotopes to carbon-12 isotopes of approximately 7.0 parts-per-thousand-versus-PDB-standard. Upon extraction of the low-purity carbon dioxide mixture from the sample of atmospheric air (e.g., via amine filtration), the low-purity carbon dioxide mixture can exhibit a second isotopic ratio of −5.0 parts-per-thousand-versus-PDB-standard. The carbon-capture process may thus decrease the concentration of carbon-13 present in the mixture.

The low-purity carbon dioxide mixture can then be purified via liquefaction to reduce a concentration of impurities (e.g., nitrogen compounds) present in the low-purity carbon dioxide mixture, thereby generating a high-purity carbon dioxide mixture. This high-purity carbon dioxide mixture can then be mixed with a stream of hydrogen gas in a methanation reactor, in the presence of a catalyst, to generate a hydrocarbon mixture. This hydrocarbon mixture can exhibit a third isotopic ratio of carbon-13 isotopes to carbon-12 isotopes of −7.0 parts-per-thousand-versus-PDB-standard. Thus, the methanation process (e.g., methanation of the high-purity carbon dioxide mixture) may again decrease the concentration of carbon-13 present in the mixture.

The resulting hydrocarbon mixture can then be purified (e.g., via liquefaction, via a set of filters) to reduce the concentration of impurities present in the hydrocarbon mixture. Then, the purified hydrocarbon mixture can be deposited in a diamond reactor containing a set of diamond seeds. The purified hydrocarbon mixture can then interact with the set of diamond seeds, in the diamond reactor, to generate a set of diamonds via chemical vapor deposition. The resulting set of diamonds can exhibit a fourth isotopic ratio of carbon-13 isotopes to carbon-12 isotopes of −3.0 parts-per-thousand-versus-PDB-standard. Thus, the CVD process may increase the concentration of carbon-13 isotopes present in the resulting diamonds compared to the hydrocarbon mixture.

Therefore, the carbon-capture process can decrease the concentration of carbon-13 present in the mixture, the methanation process can also further decrease the concentration of carbon-13 present in the mixture, and the CVD process can increase the concentration of carbon-13 isotopes present in the resulting diamonds compared to the hydrocarbon mixture and the low-purity carbon dioxide mixture.

5.1.1. Carbon-14 Isotope Concentration

In one variation, the diamond composition 100 can include a concentration of carbon-14 isotopes distinct from natural diamonds (e.g., ground-sourced diamonds). Further, by sourcing carbon from the air—rather than the ground—the diamond composition 100 is less depleted in carbon-14 than traditional lab-grown diamonds (e.g., ground-sourced HPHT and/or CVD diamonds) which may be more heavily depleted in carbon-14 compared to the diamond composition 100.

In particular, natural diamonds (e.g., ground-sourced diamonds) are heavily depleted in carbon-14 due to natural decaying of carbon-14 isotopes into carbon-13 isotopes over time. More specifically, an age of natural, ground-source diamonds generally greatly exceeds a half-life of carbon-14 isotopes, thus leading to natural diamonds (e.g., ground-sourced diamonds) enriched in carbon-13 and heavily depleted in carbon-14. However, carbon-14 is produced naturally in the atmosphere (e.g., in the upper layers of the troposphere and/or stratosphere) and therefore present in carbon dioxide in the atmosphere. Therefore, by sourcing carbon from carbon dioxide found in atmospheric air, the diamond composition 100 can exhibit a concentration of carbon-14 isotopes exceeding a concentration of carbon-14 isotopes found in natural diamonds (e.g., ground-sourced diamonds). Similarly, traditional lab-grown diamonds (e.g., ground-sourced HPHT and/or CVD diamonds) are heavily depleted in carbon-14 due to this decaying of carbon-14 isotopes into carbon-13 isotopes over time.

For example, the diamond composition 100 can include carbon sourced from air which includes a first amount of carbon-13 isotopes, a second amount of carbon-12 isotopes, and a third amount of carbon-14 isotopes. A diamond formed of the diamond composition 100 can exhibit a carbon-14 concentration within a carbon-14 concentration range (e.g., less than a carbon-13 concentration range), the carbon-14 concentration within the carbon-14 concentration range is greater than an average carbon-14 concentration exhibited by natural diamonds (e.g., ground-sourced diamonds).

Therefore, in this variation, the diamond composition 100 can exhibit a carbon-14 concentration greater than carbon-14 concentrations of both natural diamonds (e.g., ground-sourced diamonds) and traditional lab-grown diamonds (e.g., ground-sourced HPHT and/or CVD diamonds). The diamond composition 100 can thus be distinguished—and confirmed as a diamond generated from carbon sourced from air—from these natural, ground-sourced and/or traditional, lab-grown diamonds via analysis (e.g., via mass spectrometry) of the carbon-14 concentration.

5.2 Isotopic Signature Range

As shown in FIG. 3, the diamond composition 100—forming a diamond—can exhibit an isotopic signature (or "$\delta^{13}C$") defining a ratio (or "isotopic ratio") of carbon-12 isotopes to carbon-13 isotopes falling within a target isotopic signature range (e.g., between −10.0 parts-per-thousand-versus-PDB-standard and 1.0 parts-per-thousand-versus-PDB-standard, between −8.0 parts-per-thousand-versus-PDB-standard and −2.0 parts-per-thousand-versus-PDB-standard, exceeding −10.0 parts-per-thousand-versus-PDB-standard) corresponding to average isotopic signatures of natural diamonds (e.g., ground-sourced diamonds), as described above.

Additionally and/or alternatively, the diamond composition 100 can be configured to exhibit an isotopic signature defining a ratio of carbon-12 isotopes to carbon-13 isotopes falling within a comprehensive isotopic signature range (e.g., between −42.0 parts-per-thousand-versus-PDB-standard and 5.0 parts-per-thousand-versus-PDB-standard). The comprehensive isotopic signature range includes average isotopic signatures of natural diamonds (e.g., ground-sourced diamonds), and traditional lab-grown diamonds (e.g., ground-sourced HPHT and/or CVD diamonds).

However, the diamond composition 100—forming a diamond—can exhibit an isotopic signature (or "$\delta^{13}C$") defining an isotopic ratio of carbon-12 isotopes to carbon-13 isotopes falling within narrower ranges and/or exceeding or falling below a threshold ratio within this comprehensive isotopic signature range (e.g., between −42.0 parts-per-thousand-versus-PDB-standard and 5.0 parts-per-thousand-versus-PDB-standard).

5.2.1 Target Isotopic Signature Range

In one implementation, the diamond composition 100 can be generated via the method S100 and include carbon sourced from air, which includes a first amount of carbon-12 isotopes and a second amount of carbon-13 isotopes. In this implementation, the diamond composition 100 can exhibit an isotopic signature defining a first ratio of the first amount of carbon-13 isotopes to the second amount of carbon-12 isotopes within a first target range between −10.0 parts-per-thousand-versus-PDB-standard and 1.0 parts-per-thousand-versus-PDB-standard.

In one example, the diamond composition 100 can exhibit the first ratio of the first amount of carbon-13 isotopes to the second amount of carbon-12 isotopes greater than −5.0 parts-per-thousand-versus-PDB-standard and within the first target range.

In another example, the diamond composition 100 can exhibit the first ratio of the first amount of carbon-13 isotopes to the second amount of carbon-12 isotopes within a second target range, falling within the first target range, between −4.0 parts-per-thousand-versus-PDB-standard and −3.0 parts-per-thousand-versus-PDB-standard.

In yet another example, the diamond composition 100 can exhibit the first ratio of the first amount of carbon-13 isotopes to the second amount of carbon-12 isotopes within a third target range, falling within the first target range and the second target range, between −3.610 parts-per-thousand-versus-PDB-standard and −3.590 parts-per-thousand-versus-PDB-standard.

In one variation, the diamond composition 100 can exhibit an isotopic signature within an alternative target range, falling within this first target range, as a function of time, location, and/or Blocks of the method S100, further described below. The isotopic signature can vary based on the particular time period the carbon sample was extracted from air (e.g., 2010 with an isotopic signature of −5.0 parts-per-thousand-versus-PDB-standard, 2022 with an isotopic signature of −7.5 parts-per-thousand-versus-PDB-standard) and based on the geographic location the carbon sample was extracted from air (e.g., at the beach with an isotopic signature of −4.0 parts-per-thousand-versus-PDB-standard, outside of a lab facility with an isotopic signature of −3.7 parts-per-thousand-versus-PDB-standard). Additionally, the isotopic signature can vary with variations of Blocks of the method S100 such as the processes of liquefaction, CVD, and/or methanation.

5.2.2 Isotopic Signature Range+Threshold Ratio

In another variation, the diamond composition 100 can be generated via the method S100 and includes carbon sourced from air, which includes a first amount of carbon-13 isotopes, a second amount of carbon-12 isotopes, and a third amount of carbon-14 isotopes. The diamond composition 100 can also exhibit an isotopic signature defining a first ratio of the first amount of carbon-13 isotopes to the second amount of carbon-12 isotopes within a first target range between −4.0 parts-per-thousand-versus-PDB-standard and −3.0 parts-per-thousand-versus-PDB-standard.

In one example, the diamond composition 100 can exhibit the first ratio of the first amount of carbon-13 isotopes to the second amount of carbon-12 isotopes within a second target range, falling within the first target range, between −3.610 parts-per-thousand-versus-PDB-standard and −3.590 parts-per-thousand-versus-PDB-standard.

Additionally or alternatively, the diamond composition 100 can exhibit a ratio of the first amount of carbon-13 isotopes to the second amount of carbon-12 isotopes exceeding a threshold ratio, instead of falling within a target range. For example, the diamond composition 100 can exhibit the first ratio of the first amount of carbon-13 isotopes to the second amount of carbon-12 isotopes exceeding a threshold ratio of −10.0 parts-per-thousand-versus-PDB-standard.

Therefore, the diamond composition 100 can exhibit an isotopic signature within a narrow range and/or greater than a threshold ratio. Simultaneously, the isotopic signature can be greater than an average isotopic signature of both natural diamonds (e.g., ground-sourced diamonds) and traditional lab-grown diamonds (e.g., ground-sourced HPHT and/or CVD diamonds) within the comprehensive isotopic signature range.

5.3 Regulated Isotopic Signature Range

In one variation, the carbon dioxide mixture can be conveyed through a distillation column: to regulate a ratio of an amount of carbon-13 isotopes to an amount of carbon-12 isotopes to within a first target range, as described above. The resulting diamond composition 100 can thus be configured to exhibit a final ratio of a first amount of carbon-13 isotopes to a second amount of carbon-12 isotopes within a second target range corresponding to the first target range defined for the carbon dioxide mixture.

In one implementation, the resulting diamond composition 100 can be configured to exhibit an isotopic signature defining a final ratio of the first amount of carbon-13 isotopes to the second amount of carbon-12 isotopes within a target range between −60.0 parts-per-thousand-versus-PDB-standard to 5.0 parts-per-thousand-versus-PDB-standard. Additionally and/or alternatively, in yet another implementation, the resulting diamond composition 100 can be configured to exhibit an isotopic signature defining a final ratio of the first amount of carbon-13 isotopes to the second amount of carbon-12 isotopes within a target range between −10.0 parts-per-thousand-versus-PDB-standard to 5.0 parts-per-thousand-versus-PDB-standard. In each of these implementations, the target range can be expanded or decreased by adjusting parameters and operation of the distillation column.

For example, the diamond composition 100 can be configured to exhibit an isotopic signature defining a final ratio of the first amount of carbon-13 isotopes to the second amount of carbon-12 isotopes within a target range between −20.0 parts-per-thousand-versus-PDB-standard to 5.0 parts-per-thousand-versus-PDB-standard. In this example, the distillation column can include a set of levels, each level in the set of levels defining an outlet height, in a set of outlet heights, of the distillation column and corresponding to a volume, in a set of volumes, of the carbon dioxide mixture in the distillation column. Then, a first volume of the carbon dioxide mixture can be collected from a first level in the set of levels—at a maximum outlet height (e.g., top of the distillation column) in the set of outlet heights—of the distillation column. The first volume of the carbon dioxide mixture can exhibit a first target ratio of carbon-13 isotopes to carbon-12 isotopes falling within a first target range between −20.0 parts-per-thousand-versus-PDB-standard and −10.0 parts-per-thousand-versus-PDB-standard. A second volume of the carbon dioxide mixture can be collected from a second level in the set of levels—at a minimum outlet height (e.g., base of the distillation column) in the set of outlet heights—of the distillation column. The second volume of the carbon dioxide mixture can exhibit a second target ratio of carbon-13 isotopes to carbon-12 isotopes, greater than the first target ratio, and falling within a second target range between 1.0 parts-per-thousand-versus-PDB-standard and 5.0 parts-per-thousand-versus-PDB-standard.

Lastly, a third volume of the carbon dioxide mixture can be collected from a third level, between the first level and the second level, at a first outlet height between the maximum outlet height (e.g., top of the distillation column) and the minimum outlet height (e.g., base of the distillation column) of the distillation column. The third volume of the carbon dioxide mixture can define a third target ratio of carbon-13 isotopes to carbon-12 isotopes, greater than the first target ratio and less than the second target ratio, falling within a third target range between −10.0 parts-per-thousand-versus-PDB-standard and 1.0 parts-per-thousand-versus-PDB-standard. Subsequently, Blocks of the method S100 can be executed to generate the diamond composition 100 from one of and/or a mixture of these volumes of the carbon dioxide mixture to exhibit an isotopic signature defining a final ratio of the first amount of carbon-13 isotopes to the second amount of carbon-12 isotopes within the first target range between −20.0 parts-per-thousand-versus-PDB-standard to 5.0 parts-per-thousand-versus-PDB-standard.

Additionally, in the preceding example, the diamond composition 100 can be formed from a mixture of these volumes of the carbon dioxide mixture (in the preceding example) and exhibit the final ratio of the first amount of carbon-13 isotopes to the second amount of carbon-12 isotopes within a fourth target range, falling within the target range, between −4.0 parts-per-thousand-versus-PDB-standard and −3.0 parts-per-thousand-versus-PDB-standard.

In another variation, Blocks of the method S100 can be executed to generate a carbon dioxide mixture. The carbon dioxide mixture can be conveyed through the distillation column to regulate an initial ratio of carbon-13 isotopes to carbon-12 isotopes present in the carbon dioxide mixture, at the inlet of the distillation column, to within a first target range at a first outlet and a second target range at a second outlet.

For example, the carbon dioxide mixture can be conveyed through the distillation column to regulate an initial ratio of carbon-13 isotopes to carbon-12 isotopes present in the carbon dioxide mixture, at the inlet of the distillation column, to within: a first target range, at the first outlet, defining a first outlet height, of the distillation column, between −20.0 parts-per-thousand-versus-PDB-standard and −4.0 parts-per-thousand-versus-PDB-standard; and a second target range, at the second outlet, defining a second outlet height (e.g., less than the first outlet height) of the distillation column, between −4.0 parts-per-thousand-versus-PDB-standard and −3.0 parts-per-thousand-versus-PDB-standard.

Alternatively, Blocks of the method S100 can be executed to convey the carbon dioxide mixture through the distillation column to regulate a target ratio of carbon-13 isotopes to carbon-12 isotopes present in the carbon dioxide mixture to within a target range of ratios exhibited by natural diamonds (e.g., ground-sourced diamonds). For example, at a first time, the carbon dioxide mixture can be collected at a maximum outlet height (e.g., top of the distillation column) of the distillation column from the outlet to regulate the target ratio of carbon-13 isotopes to carbon-12 isotopes to within a first target range between −8.0-parts-per-thousand-versus-PDB-standard and −2.0 parts-per-thousand-versus-PDB-standard, ratios within the first target range corresponding to ratios of amounts of carbon-13 isotopes to amounts of carbon-12 isotopes exhibited by natural diamonds (e.g., ground-sourced diamonds); and, at a second time, the carbon dioxide mixture can be collected at a minimum outlet height (e.g., base of the distillation column) of the distillation column from the outlet to regulate the target ratio of carbon-13 isotopes to carbon-12 isotopes to within a second target range, falling within the first target range, between −4.0-parts-per-thousand-versus-PDB-standard and −3.0 parts-per-thousand-versus-PDB-standard.

Therefore, the distillation column can be configured to regulate amounts of carbon-13 isotopes to carbon-12 isotopes exhibiting a target ratio within a target range corresponding to outlet heights of the distillation column. Intermediate mixtures (e.g., carbon dioxide, fractionated mixtures, mixture of carbon dioxide and impurities etc.) can then be selected from a particular outlet height of the distillation column and Blocks of the method S100 can be implemented to control the final ratio of the first amount of carbon-13 isotopes to the second amount of carbon-12 isotopes within a first target range—exhibited by the diamond composition 100—corresponding to the target ratio exhibited by the intermediate mixture.

5.4 Thermal Conductivity+Isotopic Signature

Generally, thermal conductivity is proportional to the purity of a diamond (e.g., minimal to no impurities)—such that a diamond formed of the diamond composition 100 exhibits a first amount of carbon-13 isotopes (e.g., 1.0%) and a second amount of carbon-12 isotopes (e.g., 99.0%)— and measures the amount of heat that transfers through the diamond. Thermal conductivity is also a result of impurity scattering within the diamond (e.g., impurities scattered within the structure of the diamond). In particular, thermal conductivity increases due to increasing phonon energy levels within the diamond until it reaches a peak value and then decreases due to impurity scattering. Thermal conductivity is measured in units of watts-per-meter-kelvin. Thus, a distillation column and amine filtration can be configured to reduce and/or remove impurities and Blocks of the method S100 can be executed to generate a diamond formed of the diamond composition 100 with reduced impurity scattering.

Figure 8:
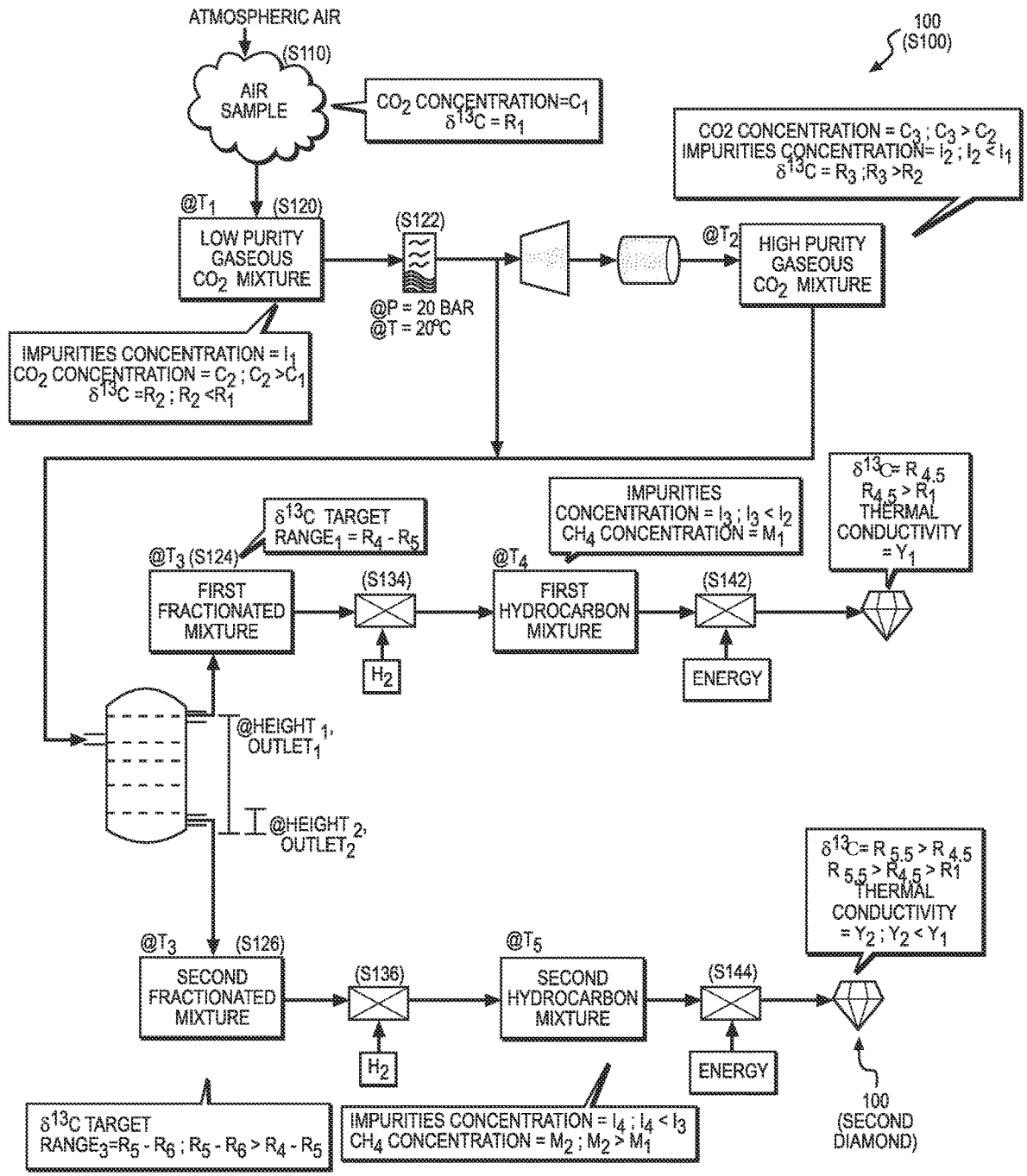
FIG. 8 is a flowchart representation of one variation of the method.

In one variation, Blocks of the method S100 can be executed to regulate amounts of carbon-13 isotopes to carbon-12 isotopes via a distillation column to exhibit a target ratio and to generate a diamond composition 100 exhibiting a target thermal conductivity, as shown in FIG. 8.

In particular, the diamond composition 100 can include carbon that includes a first amount of carbon-13 isotopes and a second amount of carbon-12 isotopes and sourced from a hydrocarbon mixture that includes hydrocarbons and formed via methanation of a carbon dioxide mixture. The carbon dioxide mixture can be conveyed through a separation unit to remove impurities and the resulting mixture can be further conveyed through a distillation column to regulate amounts of carbon-13 isotopes and carbon-12 isotopes in the mixture. The diamond composition 100 can exhibit an isotopic signature defining a final ratio of the first amount of carbon-13 isotopes to the second amount of carbon-12 isotopes within a first target range corresponding to the target ratio exhibited by the carbon dioxide mixture.

In one implementation, different subvolumes of the carbon dioxide mixture can be collected from a set of outlets— each outlet defining a particular outlet height, such that each subvolume of the carbon dioxide mixture exhibits a particular target ratio of carbon-13 isotopes to carbon-12 isotopes. Each subvolume of the carbon dioxide mixture can then be processed according to Blocks of the method S100 to form a set of diamond compositions 100 including a range of final ratios of carbon-13 isotopes to carbon-12 isotopes, and thereby exhibiting a range of thermal conductivities corresponding to the range of final ratios.

For example, the carbon dioxide mixture can include: a first subvolume exhibiting a first target ratio of carbon-13 isotopes to carbon-12 isotopes at a first outlet, in a set of outlets, of the distillation column, the first outlet defining a first outlet height; and a second subvolume exhibiting a second target ratio of carbon-13 isotopes to carbon-12 isotopes at a second outlet, in the set of outlets, of the distillation column, the second outlet defining a second outlet height less than the first outlet height. The hydrocarbon mixture includes: a third subvolume formed via methanation of the first subvolume of the carbon dioxide mixture; and a fourth subvolume formed via methanation of the second subvolume of the carbon dioxide mixture. The diamond composition 100 includes a first diamond composition: formed via chemical vapor deposition of a first diamond seed exposed to the third subvolume of the hydrocarbon mixture; and exhibiting a first isotopic signature defining a first final ratio of carbon-13 isotopes to carbon-12 isotopes. The diamond composition 100 also includes a second diamond composition: formed via chemical vapor deposition of a second diamond seed exposed to the fourth subvolume of the hydrocarbon mixture; and exhibiting a second isotopic signature defining a second final ratio of carbon-13 isotopes to carbon-12 isotopes. The first diamond composition exhibits a first thermal conductivity, and the second diamond composition exhibits a second thermal conductivity less than the first thermal conductivity.

In another example, a diamond formed of the diamond composition 100 is characterized by a first amount of thermal conductivity within a target thermal conductivity range between 2,200 watts-per-meter-kelvin and 3,000 watts-per-meter-kelvin, amounts within the target thermal conductivity range greater than amounts of thermal conductivity exhibited by natural diamonds (e.g., 2,200 watts-per-meter-kelvin, 2,400 watts-per-meter-kelvin). Accordingly, the diamond composition 100 exhibits the isotopic signature defining the final ratio of the first amount of carbon-13 isotopes to the second amount of carbon-12 isotopes within the first target range greater than −10.0 parts-per-thousand-versus-PDB-standard, ratios within the first target range corresponding to ratios of amounts of carbon-13 isotopes to amounts of carbon-12 isotopes exhibited by natural diamonds (e.g., ground-sourced diamonds).

In yet another example, a diamond formed of the diamond composition 100 is characterized by a first amount of thermal conductivity within a target thermal conductivity range between 1,000 watts-per-meter-kelvin and 2,400 watts-per-meter-kelvin, amounts within the target thermal conductivity range corresponding to ratios of amounts of thermal conductivity exhibited by natural diamonds (e.g., ground-sourced diamonds). Accordingly, the diamond composition 100 exhibits the isotopic signature defining the final ratio of the first amount of carbon-13 isotopes to the second amount of carbon-12 isotopes within the first target range between −10.0 parts-per-thousand-versus-PDB-standard and 2.0 parts-per-thousand-versus-PDB-standard.

Therefore, the thermal conductivity of the diamond composition 100 is proportional to the isotopic signature defining a ratio of carbon-13 isotopes to carbon-12 isotopes and can be regulated via purification processes (e.g., amine filtration, distillation column). The diamond composition 100 can also exhibit thermal conductivity and ratios of carbon-13 isotopes to carbon-12 isotopes greater than and/or within the range of thermal conductivities and ratios exhibited by natural diamonds (e.g., ground-sourced diamonds).

5.5 Isotopic Signature+Diamond Characteristics

In one variation, the method Sim, can be executed to generate diamonds of sufficient quality (e.g., clarity, color, cut, carat weight, carbon) with particular characteristics (e.g., size, shape, number, position, nature, grade, etc.). The carbon isotopic signature (or "$\delta^{13}C$") of each diamond, formed of the diamond composition 100, can be tested (e.g., via mass spectrometry) to verify that the diamond is generated from carbon sourced from air. The results of this test (e.g., grading report) can then be provided to a user upon purchase, which can enable the user to verify that her diamond is generated from carbon sourced from air and exhibits the particular characteristics that she selected.

More specifically, a diamond, formed of the diamond composition 100, can exhibit a particular cut, which defines how rough the diamond is sliced and the proportion and precision of the diamond's internal characteristics. The particular cut of the diamond also achieves the diamond's appearance (e.g., ideal, shallow, deep). The diamond can also exhibit a particular color (e.g., colorless, near colorless, faint yellow, very light yellow, light yellow), which is graded on an alphabetical color scale (e.g., D-Z). Additionally, the particular color of the diamond corresponds to a letter (e.g., D, colorless). The diamond can exhibit a particular clarity, which represents the clearness and/or fogginess of the diamond in terms of inclusions (or "markings") within the diamond (e.g., flawless, very, very slightly included, very slightly included, slightly included, included). The diamond can also exhibit a particular carat, which represents unit weight and is a measurement of the weight of the diamond (e.g., 0.50 carat, 0.72 carat, 1 carat, 1.5 carat, 3 carat etc.). Lastly, the diamond composition 100 of the diamond can exhibit a carbon isotopic signature defining a first ratio of a first amount of carbon-13 isotopes to a second amount of carbon-12 isotopes (e.g., −3.5 parts-per-thousand-versus-PDB-standard). The isotopic signature can be identified (e.g., via mass spectrometry) based on a piece of a diamond crystal, after the cutting process of the diamond crystal to produce the particular shape (e.g., round, emerald, pear, oval, princess, cushion, etc.) of the diamond. Thus, the diamond can exhibit particular qualities, but the carbon isotopic signature can distinguish the diamond as generated from carbon sourced from air (e.g., via mass spectrometry).

For example, the method S100 can be executed to generate a diamond formed of the diamond composition 100. The diamond can be cut to a particular shape (e.g., pear) and the isotopic signature can be detected via mass spectrometry. The generated diamond can also exhibit a colorless color, an ideal cut, and a very, very slightly included clarity rating. Later, a user may want to purchase a pendant diamond necklace with a diamond of sufficient quality (e.g., clarity, color, cut, carat weight, carbon) and particular characteristics (e.g., size, shape, number, position, nature, grade, etc.) that match the diamond generated via the method S100. The user can then select a desired shape (e.g., pear) and carat weight (e.g., 1.5 carat) for the diamond. The diamond generated via the method S100 can then be selected and inserted into the pendant diamond necklace setting. Upon purchase of the pendant diamond necklace, the user can receive a grading report of the diamond detailing the diamond's qualities, particular characteristics, and distinguish the diamond as generated from carbon sourced from air. Alternatively, the user can receive the grading report detailing the diamond's qualities and characteristics. Then, the user can test the isotopic signature of the diamond via mass spectroscopy at any chemical laboratory, and the test can distinguish the diamond as generated from carbon sourced from air.

Therefore, a diamond formed of the diamond composition 100 can be of sufficient quality (e.g., clarity, color, cut, carat weight, carbon) with particular characteristics (e.g., size, shape, number, position, nature, grade, etc.). The diamond can also exhibit an isotopic signature that can be tested during the cutting process of the diamond and can be verified, after purchase of the diamond by a user, to distinguish the diamond as generated from carbon sourced from air.

5.5.1. Diamond Characteristics vs. Natural Diamond

In another variation, a diamond formed of the diamond composition 100 can be generated via the method S100 and can be characterized by a particular size (e.g., 5.0 mm, 5.7 mm, 6.5 mm, 9.1 mm, etc.), a particular shape (e.g., round, emerald, pear, oval, princess, cushion, etc.), and a particular carat weight (e.g., 0.50 carat, 0.72 carat, 1 carat, 3 carat etc.). The isotopic signature (or "$\delta^{13}C$") of this diamond can be regulated via a distillation column to exceed an average isotopic signature of a natural, ground-sourced diamond (e.g., −5.0 parts-per-thousand-versus-PDB-standard) with the same particular size, shape, and carat weight as shown in FIGS. 2 and 3.

For example, a diamond formed of the diamond composition 100 can include carbon sourced from air, which includes a first amount of carbon-13 isotopes and a second amount of carbon-12 isotopes, and the diamond composition 100 can exhibit an isotopic signature (or "$\delta^{13}C$") defining a first ratio of the first amount of carbon-13 isotopes to the second amount of carbon-12 isotopes. The diamond can be characterized by a first shape (e.g., round), a first size (e.g., 6.5 mm), and a first weight (e.g., 1 carat) and can exhibit the isotopic signature within an isotopic signature range (e.g., between −3.610 parts-per-thousand-versus-PDB-standard and −3.590 parts-per-thousand-versus-PDB-standard). The isotopic signature within the isotopic signature range can be regulated via the distillation column to achieve an isotopic signature greater than an average isotopic signature exhibited by natural diamonds (e.g., −5.0 parts-per-thousand-versus-PDB-standard) characterized by the first shape (e.g., round), the first size (e.g., 6.5 mm), and the first weight (e.g., 1 carat).

Therefore, if a diamond formed of the diamond composition 100 and a natural diamond are characterized by the same particular shape, size, and carat weight, the diamond can exhibit a particular isotopic signature greater than an average isotopic signature of the natural diamond (e.g., ground-sourced diamond) by regulating the particular isotopic signature via the distillation column.

5.6 Location+Time

In one implementation, the diamond composition 100 defines a particular isotopic signature that can be predictably linked to a particular location and/or a particular period of time. More specifically, a model linking carbon isotopic concentrations in ambient air to time period and location of air capture can be theoretically derived based on observed weather patterns (e.g., seasonal and geographic weather patterns). This model can then be leveraged to predict: a location (e.g., a latitude) of air capture for a particular diamond formed of the diamond composition 100 (e.g., given the time period and isotopic signature); a time period (a particular season) of air capture for this particular diamond (e.g., given the location and isotopic signature); and/or an isotopic signature of the particular diamond (e.g., given the location and time period).

For example, a first instance of the diamond composition 100 can be generated from an air sample—including carbon dioxide—captured at a first geographic location (e.g., at a first latitude) during a first period of time. The first instance of the diamond composition 100 can be configured to include: a first concentration of carbon-13 isotopes; and a second concentration of carbon-12 isotopes. The first concentration of carbon-13 and the second concentration of carbon-12 can define a first isotopic signature (e.g., a ratio of carbon-13 isotopes to carbon-12 isotopes) unique to the first instance of the diamond composition 100. Further, a second instance of the diamond composition 100 can be generated from a second air sample—including carbon dioxide—captured at a second geographic location (e.g., at a second latitude) during a second period of time. The second air sample can be ingested and processed to generate a second instance of the diamond composition 100 including: a third concentration of carbon-13 greater than the first concentration of carbon-13; and a fourth concentration of carbon-12 less than the second concentration of carbon-12. The third concentration of carbon-13 and the fourth concentration of carbon-12 can define a second isotopic signature unique to the second instance of the diamond composition 100.

In the preceding example, each instance of the diamond composition 100 can be traced to the original geographic location and/or time period during which the air sample was collected for generation of the diamond composition 100 based on the isotopic signature. For example, if the first and second instance of the diamond composition 100 include carbon sourced from an air sample collected during a particular time period: the first isotopic signature and the particular time period can be inserted into the model to identify the first geographic location; and the second isotopic signature and the particular time period can be inserted into the model to identify the second geographic location.

In another example, the diamond composition 100 can be generated via the method S100 and include carbon sourced from air captured at a target location. The diamond composition 100 can form a diamond defining a diamond identifier (e.g., serial number) engraved in the diamond and configured to associate the diamond with the target time period based on a model configured to predictably link the diamond identifier (e.g., serial number) to the target time period based on observed weather patterns, as shown in FIG. 7.

In yet another example, the diamond composition 100 forms a diamond exhibiting a final ratio detectable via mass spectrometry and linked to a target location and a target time via a ratio database (e.g., database of ratios of carbon-13 isotopes to carbon-12 isotopes). The diamond composition 100 can be generated via the method S100 and includes a first amount of carbon-13 isotopes, a second amount of carbon-12 isotopes, and carbon sourced from a sample of air. The sample of air is collected at a target location and a target time during an air capture period and the final ratio of the first amount of carbon-13 isotopes to the second amount of carbon-12 isotopes is within a target range between −4.0 parts-per-thousand-versus-PDB-standard and −3.0 parts-per-thousand-versus-PDB-standard. The final ratio can then be linked to the target location and target time via a ratio database (e.g., database of ratios of carbon-13 isotopes to carbon-12 isotopes).

Therefore, a diamond owner wishing to identify a geographic location or time period of carbon capture for her diamond, formed of the diamond composition 100, may bring her diamond to any laboratory (e.g., analytical chemistry laboratory) for isotopic composition analysis of the diamond via mass spectrometry. Then, based on the isotopic composition (i.e., isotopic signature) of her diamond, the user may leverage: a known or approximate location of carbon collection to estimate a time period of carbon collection based on the model; or a known or approximate time period of carbon collection to estimate a geographic location of carbon collection for her diamond based on the model and/or ratio database. Similarly, a diamond owner (e.g., of a diamond formed of the diamond composition 100) may confirm a known location and known time period of carbon collection of a diamond by: completing isotopic composition analysis to identify a carbon isotopic signature of the diamond; and characterizing a "fit" between the known location, the known time period, and the carbon isotopic signature based on the model and/or ratio database.

5.6.1 Time-Specific Isotopic Signature

In one implementation, the methods and techniques described above can be implemented to link an intermediate product or material generated and/or consumed during generation of the diamond composition 100—such as a carbon dioxide mixture, a hydrocarbon mixture generated from the carbon dioxide mixture, etc.—that exhibits a particular isotopic signature to a particular time period during which carbon present in this intermediate product and/or material was captured from air.

For example, a carbon dioxide sample (i.e., the low-purity carbon dioxide mixture and/or the high-purity carbon dioxide mixture) can be collected during a first year (e.g., 2018) exhibiting a first isotopic ratio (e.g., 3.65 parts-per-thousand-versus-PDB-standard), and a second carbon dioxide sample can be collected during a second year (e.g., 2028 succeeding the first year by ten years) exhibiting a second isotopic ratio (e.g., 3.5 parts-per-thousand-versus-PDB-standard). Alternatively, the carbon dioxide sample (i.e., the low-purity carbon dioxide mixture and/or the high-purity carbon dioxide mixture) can be collected during two different seasons of the same year. The first carbon dioxide sample can be collected during a first season (e.g., Winter) of the first year (e.g., 2018) and exhibit a third isotopic ratio (e.g., 3.7 parts-per-thousand-versus-PDB-standard) and the second carbon dioxide sample can be collected during a second season (e.g., Summer) of the first year (e.g., 2018) and exhibit a fourth isotopic ratio (e.g., 4.0 parts-per-thousand-versus-PDB-standard). Thus, the diamond composition 100 generated from the carbon dioxide sample can be linked to a particular time period and/or a particular season within the particular time period.

In another variation, the methods and techniques described above can also be implemented to link the hydrocarbon sample (i.e., the hydrocarbon mixture generated from the carbon dioxide mixture) to a particular time period and/or a particular season within the particular time period. The hydrocarbon sample can later be traced to the particular time period (e.g., via mass spectroscopy of the isotopic signature) during which the air sample, containing carbon, was collected for generation of the diamond composition 100.

Furthermore, the diamond composition 100 can be formed to generate diamonds with a portion of carbon dioxide or hydrocarbon mixture to fulfill orders submitted by users purchasing these diamonds. The remainder of the carbon dioxide mixture and the hydrocarbon mixture can be stored for future generation of diamonds. For example, a user may place a custom order for a diamond generated from air captured during a particular time period. Then, a diamond formed of the diamond composition 100 can be generated via the method S100 from the stored carbon dioxide mixture and/or the stored hydrocarbon mixture, both exhibiting an isotopic signature matched to the particular time period. Later, a user can take their diamond to a chemical lab to identify the isotopic signature via mass spectroscopy and to test the isotopic ratio of the carbon dioxide mixture and/or the hydrocarbon mixture. The mass spectroscopy can also identify a time period of carbon capture for the carbon dioxide mixture and/or the hydrocarbon mixture based on known changes in isotopic ratio of carbon in atmospheric air over time and/or based on other known factors (e.g., location of collection).

Figure 10:
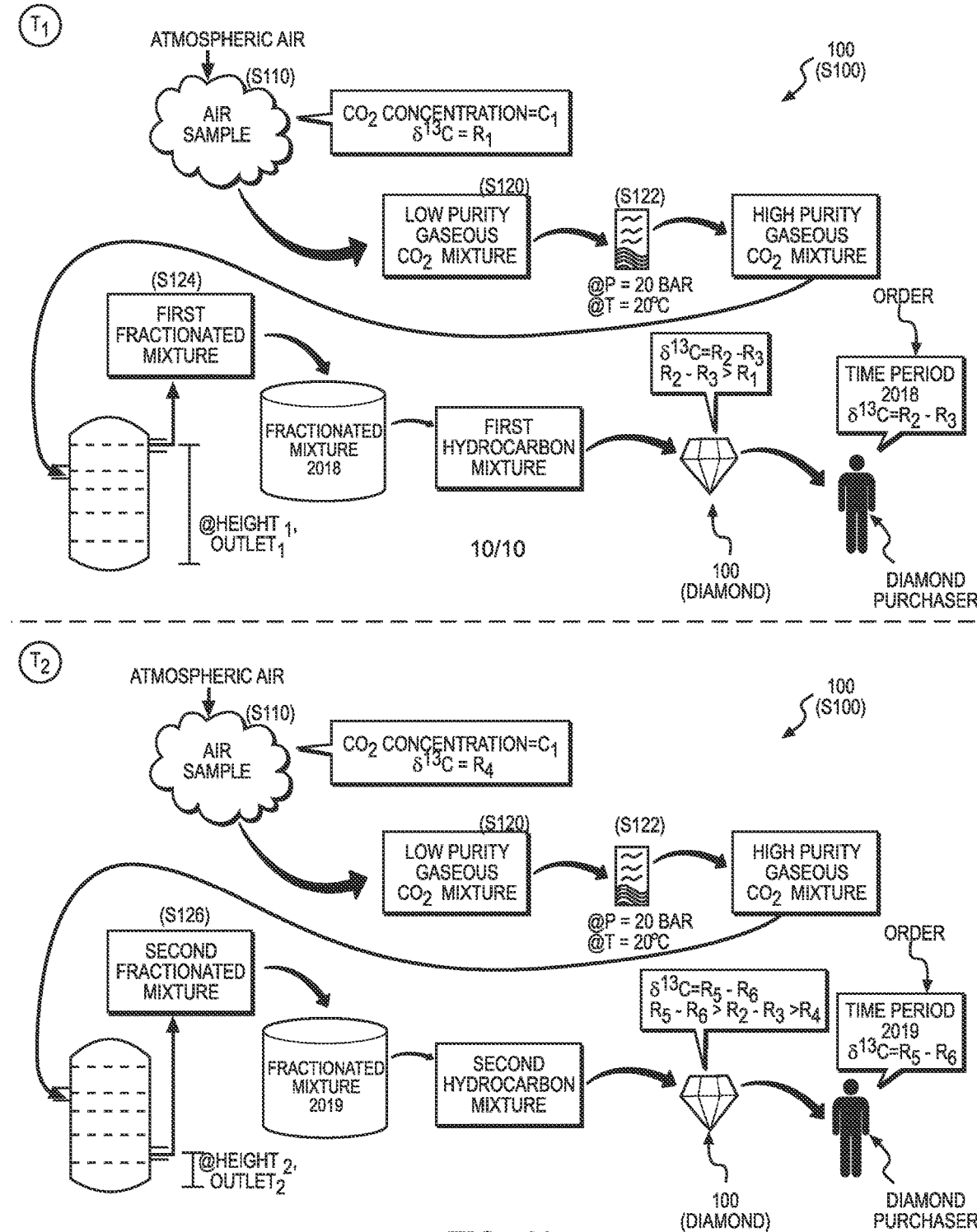
FIG. 10 is a flowchart representation of one variation of the method.

In another variation, the methods and techniques described above can be implemented to link the intermediate carbon dioxide mixture collected at the distillation column to a particular time period, as shown in FIG. 10.

In particular, Blocks of the method S100 can be executed to extract a carbon dioxide mixture from air collected during an air capture period (e.g., time period) and to convey the carbon dioxide mixture through a distillation column to regulate a target ratio of carbon-13 isotopes to carbon-12 isotopes, in the carbon dioxide mixture, to within a target range. Then, a computer system can link the target range and/or the target ratio to the air capture period (e.g., all carbon dioxide mixtures exhibiting a ratio of carbon-13 isotopes to carbon-12 isotopes within this range correspond to the air captured during the air capture period). Later, Blocks of the method S100 can be executed to extract a second carbon dioxide mixture from air collected during a subsequent air capture period and to change the ratio of carbon-13 isotopes to carbon-12 isotopes exhibited by the carbon dioxide mixture to a second target ratio within a second target range, via the distillation column. Then, the computer system can link the second target range and/or the second target ratio to the subsequent air capture period. The resulting diamond composition can exhibit a particular ratio that corresponds to the target ratio of the carbon dioxide mixture.

For example, a first volume of the carbon dioxide mixture is collected from the outlet at a first outlet height (e.g., maximum outlet height, top of the distillation column) in a set of outlet heights, of the distillation column during a target time period. The final ratio of the first amount of carbon-13 isotopes to the second amount of carbon-12 isotopes is within a second target range, falling within the first target range (e.g., −20 parts-per-thousand-versus-PDB-standard and 5.0 parts-per-thousand-versus-PDB-standard) between −4.0 parts-per-thousand-versus-PDB-standard and −3.0 parts-per-thousand-versus-PDB-standard. The diamond composition 100 forms a diamond exhibiting the final ratio within the second target range and is linked to the target time period via the ratio database (e.g., database of ratios of carbon-13 isotopes to carbon-12 isotopes).

In yet another variation, the methods and techniques described above can be implemented to link the fractionated mixtures including carbon dioxide (i.e., the first and second fractionated mixtures generated from the carbon dioxide mixture of carbon dioxide and a second concentration of impurities in Blocks S134 and S136 of the method S100) to a particular time period. For example, an amount of the first fractionated mixture including carbon dioxide can be stored in a first container (e.g., within a facility, within a laboratory) during a target time period. Then, a computer system can: generate an electronic file sample; write a timestamp for the target time period to the electronic sample file; link a first identifier arranged on the first container to the electronic sample file; and write a first diamond identifier, corresponding to the first diamond formed of the diamond composition, to the electronic sample file, as shown in FIG. 9. Thus, the diamond composition can be linked to the target time period when the amount of the first fractionated mixture was stored (via the diamond identifier).

Therefore, diamonds can be generated via the method S100 with the addition of hydrocarbons sourced from the ground and/or with the addition of a conveyed carbon dioxide mixture through a distillation column to produce diamonds from a particular time period in real time and/or in the future. The isotopic signature is also unique to each diamond and can be identified via mass spectroscopy at a chemical lab such that a user can verify the diamond as carbon sourced from air during a desired time period and/or a desired season.

5.7 Mixed Compositions

In one variation, the diamond composition 100 can be configured to include a particular mixture of carbon—such as sourced from both ambient air and/or the ground—to define an isotopic signature unique to the diamond composition 100. In this variation, the isotopic signature of the diamond composition 100 can be controlled by manipulating an amount of hydrocarbons sourced from atmospheric carbon dioxide (e.g., in air) and an amount of hydrocarbons sourced from the ground.

For example, a first diamond composition 100 can be generated from hydrocarbons sourced purely from carbon dioxide present in ambient air and including a first amount of carbon-13 isotopes and a second amount of carbon-12 isotopes. In this example, the first diamond composition 100 can be formed via chemical vapor deposition of a diamond seed; and exhibit an isotopic signature defining a first ratio of the first amount of carbon-13 isotopes to the second amount of carbon-12 isotopes within a first target range between −10.0 parts-per-thousand-versus-PDB-standard and 1.0 parts-per-thousand-versus-PDB-standard. A second diamond composition 100 can be generated from: a first amount of hydrocarbons sourced from carbon dioxide present in ambient air; and a second amount of hydrocarbons sourced from the ground, the second amount less than the first amount.

Furthermore, the second diamond composition 100 can include: a third amount of carbon-13 isotopes extracted from hydrocarbons sourced from the ground; a fourth amount of carbon-12 isotopes extracted from hydrocarbons sourced from the ground; and exhibiting a second isotopic signature defining a second ratio of the first amount of carbon-13 isotopes to the second amount of carbon-12 isotopes within a second target range greater than the first target range between −15.0 parts-per-thousand-versus-PDB-standard and −5.0 parts-per-thousand-versus-PDB-standard. Thus, by including hydrocarbons sourced from the ground in the chemical vapor deposition chamber, the resulting second diamond composition 100 can be more depleted in carbon-13 than the first diamond composition 100.

Finally, in this example, a third diamond composition 100 can be generated from: a third amount of hydrocarbons sourced from carbon dioxide present in ambient air; and a fourth amount of hydrocarbons sourced from the ground, the fourth amount greater than the first amount. In this example, the third diamond composition 100 can define a second ratio of carbon-13 isotopes to carbon-12 isotopes (i.e., an isotopic signature) between −40.0 parts-per-thousand-versus-PDB-standard and −10.0 parts-per-thousand-versus-PDB-standard. Thus, by including more hydrocarbons sourced from the ground than sourced from the air in the chemical vapor deposition chamber, the resulting third diamond composition 100 can be more heavily depleted in carbon-13 than the first and second diamond compositions 100.

Consequently, by mixing the hydrocarbon mixture formed via the method S100 with additional hydrocarbons sourced from the ground, a concentration of impurities—such as nitrogen or nitrogen compounds—in the hydrocarbon mixture can be reduced prior to depositing the hydrocarbon mixture in the diamond reactor.

Additionally or alternatively, the diamond composition 100 can be similarly configured to include a particular mixture of carbon—such as sourced from both ambient air and/or the ground—to define an isotopic signature unique to the diamond composition 100. However, in this variation, the carbon can be sourced from ambient air at a target time and/or from the ground at a target location. The isotopic signature can be controlled by manipulating an amount of hydrocarbons sourced from atmospheric carbon dioxide (e.g., in air) at the target time and an amount of hydrocarbons sourced from the ground at the target location to link the isotopic signature to the target time and/or target location.

For example, a diamond composition 100 can be generated from: a first amount of hydrocarbons sourced from carbon dioxide present in ambient air at a target time (e.g., year 2000); and a second amount of hydrocarbons sourced from the ground at a target location (e.g., North America), the second amount less than the first amount. The diamond composition 100 can also include a first amount of carbon-13 isotopes extracted from hydrocarbons sourced from the ground at the target location (e.g., North America); a second amount of carbon-12 isotopes extracted from hydrocarbons sourced from the ground at the target location (e.g., North America) and exhibiting an isotopic signature defining a ratio of the first amount of carbon-13 isotopes to the second amount of carbon-12 isotopes within a target range between −15.0 parts-per-thousand-versus-PDB-standard and −10.0 parts-per-thousand-versus-PDB-standard. Thus, by including hydrocarbons sourced from the ground in the chemical vapor deposition chamber, the resulting diamond composition 100 can be more depleted in carbon-13 and distinguishable as a diamond generated from carbon sourced from the air and the ground in North America during the year 2000.

Therefore, by including carbon sourced from both ambient air and the ground, the carbon isotopic signature of the diamond composition 100 can be manipulated based on varying concentrations of carbon-13 isotopes and carbon-12 isotopes in carbon sourced from the air and ground, thereby enabling generation of diamonds—formed of the diamond composition 100—exhibiting an isotopic signature unique to a particular diamond or batch of diamonds linked to a target time period and/or a target location.

6. EXAMPLES

In the following examples, the diamond composition 100 was generated according to the method S100 and the isotopic ratio of carbon-13 to carbon-12 was measured.

In particular, for each example, an air sample (e.g., a volume of atmospheric air) was ingested to extract a volume of a first carbon dioxide mixture (e.g., a low-purity gaseous carbon dioxide mixture) from the air sample via amine filtration and/or additional heating techniques (e.g., to remove carbon dioxide from a filter). The first carbon dioxide mixture was then purified via liquefaction, within a set temperature range (e.g., less than 31 degrees Celsius) and a set pressure range (e.g., less than 73 bar), to remove impurities (e.g., nitrogen) from the first carbon dioxide mixture, thus generating a second carbon dioxide mixture (e.g., a liquid, high-purity carbon dioxide mixture) exhibiting a lower concentration of impurities than the first carbon dioxide mixture.

The second carbon dioxide mixture was then converted from a liquid state (e.g., after liquefaction) to a gaseous state via an expander. The second carbon dioxide mixture was then run through an absorption cartridge at a set flowrate (e.g., between 8 Liters/minute and 12 Liters/minute) to remove impurities (e.g., nitrogen oxides, ammonia) from the second carbon dioxide mixture.

The second carbon dioxide mixture was then mixed with a stream of hydrogen gas, in the presence of a catalyst, to generate a first hydrocarbon mixture, including methane, via methanation of the second carbon dioxide mixture in a methanation reactor. A stream of argon was also cycled through the methanation reactor to prevent introduction of impurities (e.g., nitrogen) into the methanation reactor.

The first hydrocarbon mixture was passed through a set of filters configured to collect impurities—such as compounds containing nitrogen (e.g., nitric oxide, nitrogen dioxide), hydrogen, carbon dioxide, argon, or other gases (e.g., other than methane)—present in the first hydrocarbon mixture, thereby generating a second hydrocarbon mixture exhibiting a lower concentration of impurities than the first hydrocarbon mixture. The second hydrocarbon mixture was then passed through a compressor to further reduce all non-hydrocarbon gases present in the second hydrocarbon mixture and a dryer to reduce moisture (e.g., water) present in the second hydrocarbon mixture.

The second hydrocarbon mixture was then deposited in a diamond reactor containing a set of diamond seeds to generate the diamond composition 100 via chemical vapor deposition. The diamond reactor was heated to temperatures within a set temperature range (e.g., greater than 800 degrees Celsius) to dispel carbon ions from the second hydrocarbon mixture and into the set of diamond seeds. The resulting set of diamonds—formed of the diamond composition 100—were collected and stored for further analysis.

6.1 Results

For each example, to analyze the carbon isotopic ratio of the diamond composition 100, a mass-to-charge ratio of both the carbon-12 isotope and the carbon-13 isotope were collected via isotope ratio mass spectrometry or ("IRMS"). The concentrations of each isotope were then estimated based on the measured mass-to-charge ratios for each isotope.

The carbon isotopic signature (i.e., $\delta^{13}C$) of the diamond composition 100 was then estimated according to Equation 1 below.

$$\delta^{13}C = \left( \frac{\left(\frac{^{13}C}{^{12}C}\right)_{sample}}{\left(\frac{^{13}C}{^{12}C}\right)_{standard}} - 1 \right) \times 1000\%_0 \quad \text{(EQUATION 1)}$$

The Pee Dee Belemnite (or "PDB") reference was used as the standard such that the ratio of carbon-13 isotopes to carbon-12 isotopes for the standard was approximately 0.01123720.

In each example, each diamond tested includes: a first amount of carbon-13 isotopes; and a second amount of carbon-12 isotopes.

6.1.1 Example 1

In Example 1, as shown in FIG. 2, diamonds formed of the diamond composition 100 exhibited an average isotopic ratio (i.e., $\delta^{13}C$) of the first amount of carbon-13 isotopes to the second amount of carbon-12 isotopes of −3.50 parts-per-thousand-versus-PDB-standard with a standard deviation of 0.015 parts-per-thousand-versus-PDB-standard.

As shown in FIG. 2, the synthetic CVD diamond exhibited an isotopic ratio (i.e., $\delta^{13}C$) of the first amount of carbon-13 isotopes to the second amount of carbon-12 isotopes of −52.445 parts-per-thousand-versus-PDB-standard with a standard deviation of 0.015 parts-per-thousand-versus-PDB-standard. The synthetic HPHT diamond exhibited an isotopic ratio (i.e., $\delta^{13}C$) of the first amount of carbon-13 isotopes to the second amount of carbon-12 isotopes of −19.709 parts-per-thousand-versus-PDB-standard with a standard deviation of 0.008 parts-per-thousand-versus-PDB-standard.

As shown in FIG. 2, approximately 95 percent of Peridotitic diamonds (i.e., natural diamonds, ground-sourced diamonds), including silicate inclusions, exhibited an isotopic ratio (i.e., $\delta^{13}C$) of the first amount of carbon-13 isotopes to the second amount of carbon-12 isotopes between 2.0 parts-per-thousand-versus-PDB-standard and 8.0 parts-per-thousand-versus-PDB-standard. Further, approximately 75 percent of Eclogitic diamonds (i.e., natural diamonds, ground-sourced diamonds), including silicate inclusions, exhibited an isotopic ratio (i.e., $\delta^{13}C$) of the first amount of carbon-13 isotopes to the second amount of carbon-12 isotopes between −2.0 parts-per-thousand-versus-PDB-standard and −8.0 parts-per-thousand-versus-PDB-standard.

As shown in FIG. 1, the natural diamonds—Peridotitic and Eclogitic—define a target isotopic signature range between 2.0 parts-per-thousand-versus-PDB-standard and −8.0 parts-per-thousand-versus-PDB-standard. The diamond composition 100 exhibits a carbon isotopic signature within this target isotopic signature range. Further, the diamond composition 100 exhibits a carbon isotopic signature that is less depleted (or more enriched) in carbon-13 isotopes than the HPHT and CVD diamonds. The HPHT diamonds exhibit a carbon isotopic signature outside of the target isotopic signature range and are more depleted in carbon-13 than the diamond composition 100. The CVD diamonds also exhibit a carbon isotopic signature outside of the target isotopic signature range and are more depleted in carbon-13 than both the diamond composition 100 and the HPHT diamonds.

Therefore, while the lab-grown HPHT and CVD diamonds may be detectably distinct from natural, ground-sourced diamonds (e.g., Eclogitic and/or Peridotitic diamonds), the diamond composition 100 is not detectably (e.g., via mass spectroscopy) distinct from the natural, ground-sourced diamonds (e.g., based on the corresponding carbon isotopic signatures).

6.1.2 Example 2

In Example 2, as shown in FIG. 3, diamonds formed of the diamond composition 100 exhibited an average isotopic ratio (i.e., $\delta^{13}C$) of the first amount of carbon-13 isotopes to the second amount of carbon-12 isotopes of −3.50 parts-per-thousand-versus-PDB-standard with a standard deviation of 0.015 parts-per-thousand-versus-PDB-standard.

As shown in FIG. 3, the synthetic CVD diamond exhibited an isotopic ratio (i.e., $\delta^{13}C$) of the first amount of carbon-13 isotopes to the second amount of carbon-12 isotopes of −52.2 parts-per-thousand-versus-PDB-standard with a standard deviation of 0.015 parts-per-thousand-versus-PDB-standard. The synthetic HPHT diamond exhibited an isotopic ratio (i.e., $\delta^{13}C$) of the first amount of carbon-13 isotopes to the second amount of carbon-12 isotopes of −17.4 parts-per-thousand-versus-PDB-standard with a standard deviation of 0.008 parts-per-thousand-versus-PDB-standard.

Therefore, while the lab-grown HPHT and CVD diamonds may be detectably distinct from natural, ground-sourced diamonds (e.g., Eclogitic and/or Peridotitic diamonds), the diamond composition 100 is not detectably (e.g., via mass spectroscopy) distinct from the natural, ground-sourced diamonds based on the corresponding carbon isotopic signatures.

However, in one variation, as described above, the diamond composition 100 can be configured to exhibit an isotopic signature—defining a ratio (or "isotopic ratio") of carbon-13 isotopes to carbon-12 isotopes—outside of a target isotopic signature range (e.g., between 2.0 parts-per-thousand-versus-PDB-standard and −8.0 parts-per-thousand-versus-PDB-standard) defined by the natural diamonds by conveying the upstream carbon dioxide mixture through a distillation column configured to regulate the carbon isotopic signature of the carbon dioxide mixture.

As a person skilled in the art will recognize from the previous detailed description and from the figures and claims, modifications and changes can be made to the embodiments of the invention without departing from the scope of this invention as defined in the following claims.

We claim:

1. A diamond composition:
comprising carbon sourced from air and comprising:
a first amount of carbon-13 isotopes; and
a second amount of carbon-12 isotopes;
formed within a diamond reactor via chemical vapor deposition of a diamond seed in the presence of a gaseous hydrocarbon mixture:
comprising hydrocarbons comprising carbon sourced from air; and
formed via methanation of a carbon dioxide mixture extracted from air and comprising carbon dioxide and impurities; and
exhibiting an isotopic signature defining a first ratio of the first amount of carbon-13 isotopes to the second amount of carbon-12 isotopes within a first target range between −10.0 parts-per-thousand-versus-PDB-standard and 1.0 parts-per-thousand-versus-PDB-standard.

2. The diamond composition of claim 1:
further comprising, a third amount of carbon-14 isotopes; and
wherein a diamond formed of the diamond composition exhibits a carbon-14 concentration within a carbon-14 concentration range, the carbon-14 concentration within the carbon-14 concentration range greater than an average carbon-14 concentration exhibited by natural diamonds.

3. The diamond composition of claim 1, wherein the first ratio falls within a second target rate range between −8.0 parts-per-thousand-versus-PDB-standard and −2.0 parts-per-thousand-versus-PDB-standard, ratios within the second target range corresponding to ratios of amounts of carbon-13 isotopes to amounts of carbon-12 isotopes exhibited by natural diamonds.

4. The diamond composition of claim 3, wherein a diamond formed of the diamond composition:
is characterized by a first shape, a first size, and a first weight; and
exhibits the isotopic signature within an isotopic signature range, the isotopic signature within the isotopic signature range greater than an average isotopic signature exhibited by natural diamonds characterized by the first shape, the first size, and the first weight.

5. The diamond composition of claim 1, wherein the first ratio of the first amount of carbon-13 isotopes to the second amount of carbon-12 isotopes is greater than −5.0 parts-per-thousand-versus-PDB-standard and within the first target range.

6. The diamond composition of claim 1, wherein the first ratio of the first amount of carbon-13 isotopes to the second amount of carbon-12 isotopes is within a second target range, falling within the first target range, between −4.0 parts-per-thousand-versus-PDB-standard and −3.0 parts-per-thousand-versus-PDB-standard.

7. The diamond composition of claim 6, wherein the first ratio of the first amount of carbon-13 isotopes to the second amount of carbon-12 isotopes is within a third target range, falling within the first target range and the second target range, between −3.610 parts-per-thousand-versus-PDB-standard and −3.590 parts-per-thousand-versus-PDB-standard.

8. The diamond composition of claim 1, wherein the diamond composition forms a diamond configured to insert into an ornamental setting to form a diamond product wearable by a user.

9. The diamond composition of claim 1, wherein the diamond composition forms a diamond exhibiting a type IIA diamond type and configured to insert into a jewelry setting to generate a diamond product wearable by a user.

10. The diamond composition of claim 1:
wherein carbon of the diamond composition is sourced from air captured at a target location; and
wherein the diamond composition forms a diamond defining a diamond identifier engraved in the diamond and configured to associate the diamond with the target location, the diamond identifier linked to the target location and stored in a diamond identifier database.

11. The diamond composition of claim 1:
wherein carbon of the diamond composition is sourced from air captured during a target time period;
wherein the diamond composition forms a diamond defining a diamond identifier engraved in the diamond and configured to associate the diamond with the target time period via a model; and
wherein the model is configured to link the diamond identifier to the target time period based on observed weather patterns.

12. The diamond composition of claim 1, further comprising:
a third amount of carbon-13 isotopes extracted from hydrocarbons sourced from ground;
a fourth amount of carbon-12 isotopes extracted from hydrocarbons sourced from ground; and
exhibiting a second isotopic signature defining a second ratio of the third amount of carbon-13 isotopes to the fourth amount of carbon-12 isotopes within a second target range greater than the first target range.

13. A diamond composition:
comprising carbon sourced from air and comprising:
a first amount of carbon-13 isotopes;
a second amount of carbon-12 isotopes; and
a third amount of carbon-14 isotopes;
formed via chemical vapor deposition of a diamond seed; and
exhibiting an isotopic signature comprising a ratio of the first amount of carbon-13 isotopes to the second amount of carbon-12 isotopes within a target range between −4.0 parts-per-thousand-versus-PDB-standard and −3.0 parts-per-thousand-versus-PDB-standard; and
exhibiting a carbon-14 concentration within a carbon-14 concentration range greater than an average carbon-14 concentration exhibited by natural diamonds.

14. The diamond composition of claim 13, wherein the ratio of the first amount of carbon-13 isotopes to the second amount of carbon-12 isotopes is within a second target range, falling within the first target range, between −3.610 parts-per-thousand-versus-PDB-standard and −3.590 parts-per-thousand-versus-PDB-standard.

15. The diamond composition of claim 13, wherein a diamond formed of the diamond composition exhibits a carbon-13 concentration within a carbon-13 concentration range, the carbon-13 concentration within the carbon-13 concentration range greater than an average carbon-13 concentration exhibited by natural diamonds.

16. A diamond composition:
comprising carbon sourced from air and comprising:
 a first amount of carbon-13 isotopes; and
 a second amount of carbon-12 isotopes;
formed via chemical vapor deposition of a diamond seed exposed to a gaseous hydrocarbon mixture:
 comprising hydrocarbons comprising carbon sourced from air; and
 formed via methanation of a carbon dioxide mixture extracted from a sample of air and comprising carbon dioxide and impurities; and
exhibiting an isotopic signature defining a first ratio of the first amount of carbon-13 isotopes to the second amount of carbon-12 isotopes exceeding a threshold ratio of −10.0 parts-per-thousand-versus-PDB-standard.

17. The diamond composition of claim 16, wherein the diamond composition excludes ground-sourced carbon.

18. The diamond composition of claim 16:
wherein the carbon dioxide mixture exhibits an initial ratio of initial amounts of carbon-13 isotopes to carbon-12 isotopes;
wherein the gaseous hydrocarbon mixture exhibits a secondary ratio of secondary amounts of carbon-13 isotopes to carbon-12 isotopes and is less than the initial ratio of the carbon dioxide mixture; and
wherein the first ratio of the diamond composition is greater than the initial ratio of the carbon dioxide mixture and the secondary ratio of the gaseous hydrocarbon mixture.

19. A diamond composition:
comprising carbon sourced from air and comprising:
 a first amount of carbon-13 isotopes;
 a second amount of carbon-12 isotopes; and
 a third amount of carbon-14 isotopes;
formed via chemical vapor deposition of a diamond seed;
exhibiting an isotopic signature defining a first ratio of the first amount of carbon-13 isotopes to the second amount of carbon-12 isotopes within a first target range between −10.0 parts-per-thousand-versus-PDB-standard and 1.0 parts-per-thousand-versus-PDB-standard; and
exhibiting a carbon-14 concentration within a carbon-14 concentration range and greater than an average carbon-14 concentration exhibited by natural diamonds.

20. A diamond composition:
comprising carbon sourced from air, captured at a target location, and comprising:
 a first amount of carbon-13 isotopes; and
 a second amount of carbon-12 isotopes;
formed via chemical vapor deposition of a diamond seed;
exhibiting an isotopic signature defining a first ratio of the first amount of carbon-13 isotopes to the second amount of carbon-12 isotopes within a first target range between −10.0 parts-per-thousand-versus-PDB-standard and 1.0 parts-per-thousand-versus-PDB-standard; and
forming a diamond defining a diamond identifier engraved in the diamond and configured to associate the diamond with the target location, the diamond identifier linked to the target location and stored in a diamond identifier database.

21. A diamond composition:
comprising carbon sourced from air and comprising:
 a first amount of carbon-13 isotopes; and
 a second amount of carbon-12 isotopes;
formed via chemical vapor deposition of a diamond seed; and
exhibiting an isotopic signature defining a first ratio of the first amount of carbon-13 isotopes to the second amount of carbon-12 isotopes within a first target range between −10.0 parts-per-thousand-versus-PDB-standard and 1.0 parts-per-thousand-versus-PDB-standard.

* * * * *